United States Patent
Ariizumi et al.

(10) Patent No.: US 10,517,948 B2
(45) Date of Patent: Dec. 31, 2019

(54) ANTI-DC-HIL ANTIBODIES FOR CANCER DIAGNOSIS, PROGNOSIS AND THERAPY

(71) Applicant: The Board of Regents of the University of Texas System, Austin, TX (US)

(72) Inventors: Kiyoshi Ariizumi, Dallas, TX (US); Ponciano Cruz, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/556,985

(22) PCT Filed: Mar. 9, 2016

(86) PCT No.: PCT/US2016/021472
§ 371 (c)(1),
(2) Date: Sep. 8, 2017

(87) PCT Pub. No.: WO2016/145022
PCT Pub. Date: Sep. 15, 2016

(65) Prior Publication Data
US 2018/0064809 A1  Mar. 8, 2018

Related U.S. Application Data

(60) Provisional application No. 62/131,473, filed on Mar. 11, 2015.

(51) Int. Cl.
| | | |
|---|---|---|
| *G01N 33/53* | (2006.01) | |
| *G01N 33/574* | (2006.01) | |
| *A61K 39/395* | (2006.01) | |
| *C07K 16/28* | (2006.01) | |
| *C07K 16/30* | (2006.01) | |
| *C12Q 1/68* | (2018.01) | |
| *C12Q 1/6886* | (2018.01) | |
| *A61K 45/06* | (2006.01) | |
| *A61K 35/15* | (2015.01) | |
| *A61K 39/00* | (2006.01) | |

(52) U.S. Cl.
CPC ............ *A61K 39/395* (2013.01); *A61K 35/15* (2013.01); *A61K 45/06* (2013.01); *C07K 16/28* (2013.01); *C07K 16/2827* (2013.01); *C07K 16/30* (2013.01); *C12Q 1/68* (2013.01); *C12Q 1/6886* (2013.01); *G01N 33/5743* (2013.01); *A61K 2039/505* (2013.01); *A61K 2039/545* (2013.01); *C07K 2317/76* (2013.01); *C07K 2319/30* (2013.01); *C12Q 2600/118* (2013.01); *C12Q 2600/158* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 8,846,873 B2 | 9/2014 | Xiao et al. |
|---|---|---|
| 2002/0151486 A1 | 10/2002 | Popoff et al. |
| 2003/0202938 A1 | 10/2003 | Rameshwar |
| 2009/0297479 A1 | 12/2009 | Ariizumi et al. |
| 2012/0177664 A1 | 7/2012 | Yokoseki et al. |
| 2014/0057306 A1 | 2/2014 | Hryhorenko et al. |
| 2014/0370001 A1 | 12/2014 | Mollick et al. |

FOREIGN PATENT DOCUMENTS

| CN | 1560082 | 1/2005 |
|---|---|---|
| WO | WO 1999-009055 | 2/1999 |
| WO | WO 2006-111019 | 10/2006 |
| WO | WO 2007-053718 | 5/2007 |
| WO | WO 2012-017085 | 2/2012 |
| WO | WO 2013-026059 | 2/2013 |
| WO | WO 2014-022680 | 2/2014 |

OTHER PUBLICATIONS

Turrentine et al (Journal of Investigative Dermatology, Jul. 17, 2014, 134:2839-2842, IDS).*
Chung et al (Journal of Investigative Dermatology, Jul. 10, 2014, 134:2784-2794, IDS).*
Chung et al (J Investigative Dermatology, 2014, 134:2784-2794).*
Chung et al (J Investigative Dermatology, 2014, 134:2784-2794) Supplementary Infromation.*
Turrentine et al (J Investigative Dermatology, 2014, 134:2839-2842).*
Chung et al (J of Immunology, 2014, 192:2576-2584).*
Chung et al., "DC-HIL is a negative regulator of T lymphocyte activation," *Blood*, 109(10):4320-4327, 2007.
Chung et al., "DC-HIL-Expressing Myelomonocytic Cells Are Critical Promoters of Melanoma Growth," *J. Invest. Dermatol.*, 134:2784-2794, 2014.
Chung et al., "Syndecan-4 Mediates the Coinhibitory Function of DC-HIL on T Cell Activation," *J. Immunol.*, 179(9):5778-5784, 2007.
Gabrilovich and Nagaraj, "Myeloid-derived-suppressor cells as regulators of the immune system," *Nat. Rev. Immunol.*, 9(3):162-174, 2009.
Han et al., "Immunoglobulin Kappa Light Chain, Partial [Mus musculus]," National Center for Biotechnology Information, GenBank Accession No. ABC86098.1; downloaded from the internet <http://www.ncbi.nlm.nih.gov/protein/85838331> on May 20, 2015, p. 1; submitted Mar. 23, 2006.
Hara et al., "Immunoglobulin Kappa Heavy Chain, Partial [Mus musculus]," National Center for Biotechnology Information, GenBank Accession No. BAU30262.1; downloaded from the internet <http://www.ncbi.nlm.nih.gov/protein/974136482> on May 21, 2015, pp. 1-2; submitted Sep. 20, 2013.

(Continued)

*Primary Examiner* — Laura B Goddard
(74) *Attorney, Agent, or Firm* — Parker Highlander PLLC

(57) ABSTRACT

The present disclosure is directed to antibodies that bind to DC-HIL on the surface of myeloid-derived suppressor cells, and thus antagonize the T cell suppressor function of these cells, as well as their use in diagnosing and treating cancers such as melanoma.

8 Claims, 21 Drawing Sheets
Specification includes a Sequence Listing.

(56) References Cited

OTHER PUBLICATIONS

International Preliminary Report Patentability issued in corresponding PCT Application No. PCT/US2016/021472, dated Sep. 21, 2017.
International Search Report and Written Opinion issued in corresponding PCT Application No. PCT/US2016/021472, dated Jun. 29, 2016.
Li et al., "*Hyphomonas beringensis* sp. nov. and *Hyphomonas chukchiensis* sp. nov., Isolated from Surface Seawater of the Bering Sea and Chukchi Sea," Antonie van Leeukwenhoek, 106(4):657-665, 2014.
Metz et al., "Role of human HGFIN/nmb in breast cancer," *Breast Cancer Res.*, 9(5):R58, 2007.
Rose et al., "Osteoactivin/HGFIN: Is it a Tumor Suppressor or Mediator of Metastasis in Breast Cancer?" *Breast Cancer Res.*, 9(403):1-2, 2007.
Safadi et al., "Cloning and characterization of osteoactivin, a novel cDNA expressed in osteoblasts," *J. Cell. Biochem.*, 84(1):12-26, 2002.
Shikano et al., "Molecular Cloning of a Dendritic Cell-associated Transmembrane Protein, DC-HIL, That Promotes RGD-dependent Adhesion of Endothelial Cells through Recognition of Heparan Sulfate Proteoglycans," *J. Biol. Chem.*, 276(11):8125-8134, 2001.
Tomihari et al., "DC-HIL/Glycoprotein Nmb Promotes Growth of Melanoma in Mice by Inhibiting the Activation of Tumor-Reactive T Cells," *Cancer Res.*, 70(14):5778-5787, 2010.
Turrentine et al., "DC-HIL$^+$ CD14$^+$ HLA-DR$^{no/low}$ Cells Are a Potential Blood Marker and Therapeutic Target for Melanoma," *J. Invest. Dermatol.*, 134(11):2839-2842, 2014.
Weterman et al., "nmb, a Novel Gene, is Expressed in Low-Metastatic Human Melanoma Cell Lines and Xenografts," *Int. J. Cancer*, 60(1):73-81, 1995.

\* cited by examiner

| Cancer Stages | Patients (n) | Average Age (Yr.) | Gender |
| --- | --- | --- | --- |
| Healthy Donors | 21 | 57±11 | M(11)/F(10) |
| Dysplastic Nevi | 12 | 58±10 | M(6)/F(6) |
| Stage 0 Melanoma | 26 | 62±12 | M(15)/F(11) |
| Stage I/II Melanoma | 7 | 64±10 | M(3)/F(4) |
| Stage III Melanoma | 15 | 61±12 | M(7)/F(8) |
| Stage IV Melanoma | 14 | 63±14 | M(7)/F(7) |

FIG. 13

| Pat # | Age | Gender | Months after resection | % MDSCs /PBMC | % DC-HIL⁺ /MDSCs | % DC-HIL⁺ MDSCs/ PBMC |
|---|---|---|---|---|---|---|
| M67 | 61 | M | 0 | 5.1 | 98.7 | 5.0 |
| | | | 1 | 5.1 | 60.8 | 3.1 |
| | | | 3 | 4.2 | 40.2 | 1.7 |
| | | | 6 | 3.6 | 39.9 | 1.4 |
| M68 | 86 | M | 0 | 7 | 97.4 | 6.8 |
| | | | 1 | 7 | 72.8 | 5.1 |
| | | | 3 | 6.7 | 59.2 | 4.0 |
| | | | 6 | 1.2 | 41.5 | 0.5 |
| M69 | 78 | M | 0 | 3.7 | 64.7 | 2.4 |
| | | | 1 | 3.7 | 45.7 | 1.7 |
| | | | 3 | 1.8 | 3.2 | 0.1 |
| M70 | 58 | M | 0 | 11.5 | 40.5 | 4.7 |
| | | | 1 | 4.6 | 10 | 0.5 |
| | | | 3 | 3.9 | 11.2 | 0.4 |
| M71 | 73 | M | 0 | 2.9 | 63.5 | 1.8 |
| | | | 1 | 6.5 | 7.6 | 0.5 |
| | | | 3 | 4.1 | 34.2 | 1.4 |
| | | | 6 | 0.2 | 8.1 | 0.0 |
| M72 | 66 | M | 0 | 18.3 | 69.9 | 12.8 |
| | | | 1 | 4.6 | 26.2 | 1.2 |
| | | | 3 | 1.2 | 4.6 | 0.1 |
| M74 | 72 | M | 0 | 2.6 | 28 | 0.7 |
| | | | 1 | 2.1 | 3.2 | 0.1 |
| | | | 3 | 6.3 | 7.9 | 0.5 |
| M82 | 75 | F | 0 | 1.3 | 25.6 | 0.3 |
| | | | 1 | 0.6 | 6.7 | 0.0 |
| | | | 3 | 1.7 | 19.4 | 0.3 |
| M83 | 73 | M | 0 | 1.2 | 11.6 | 0.1 |
| | | | 1 | 2.1 | 36.4 | 0.8 |
| | | | 3 | 1.3 | 31 | 0.4 |

FIG. 14

| Subject # | Age | Gender | Months after first blood draw | % MDSCs /PBMC | % DC-HIL⁺ /MDSCs | % DC-HIL⁺ MDSCs/PBMC |
|---|---|---|---|---|---|---|
| N1 | 58 | F | 0 | 1 | 12.8 | 0.1 |
|  |  |  | 1 | 1.4 | 4.4 | 0.1 |
|  |  |  | 3 | 2.1 | 2.9 | 0.1 |
|  |  |  | 6 | 1.2 | 20.7 | 0.2 |
| N2 | 74 | M | 0 | 0.6 | 8.9 | 0.1 |
|  |  |  | 1 | 0.4 | 0.5 | 0.0 |
|  |  |  | 3 | 0.2 | 14.1 | 0.0 |
| N3 | 61 | M | 0 | 1.3 | 8.9 | 0.1 |
|  |  |  | 1 | 1.6 | 4.7 | 0.1 |
|  |  |  | 3 | 1.5 | 19.7 | 0.3 |
| N4 | 62 | F | 0 | 1.1 | 8.9 | 0.1 |
|  |  |  | 1 | 0.9 | 6.1 | 0.1 |
| N5 | 48 | M | 0 | 2.7 | 15.2 | 0.4 |
|  |  |  | 1 | 1.7 | 18.9 | 0.3 |
| N6 | 55 | F | 0 | 4.1 | 17.2 | 0.7 |
|  |  |  | 1 | 3.8 | 13.2 | 0.5 |

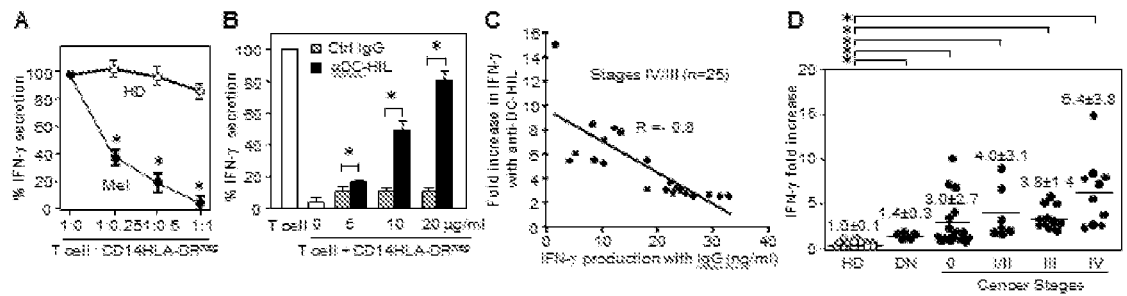
FIGS. 17A-D
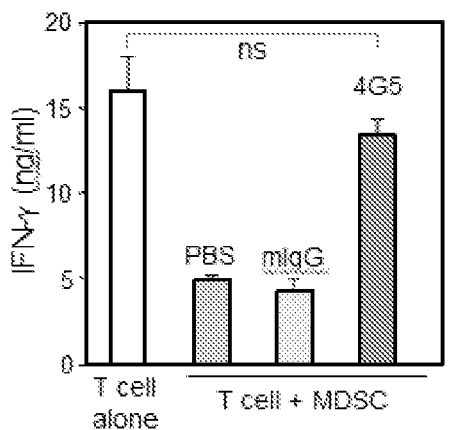
FIG. 18

3D5 V$_H$ region:

CAGGTCCAACTGCAGCAGTCTGGGGCTGAACTGGTGAAGCCTGGGACTTCAGTGAA
GTTGTCCTGCAAGGCTTCTGGCTACACCTTCACCAACTACTATATGTACTGGGTGAA
ACAGAGGCCTGGACAAGGCCTTGAGTGGATTGGAGAGATTAATACTAGAAATGGTG
GTAATAGGTTCAATGAGAAGTTCAAGAACAAGGCCATATTGACTGTAGACAAATCC
TCCAACACAGCATACATACAAGTCAGCAGCCTGACATCTGAGGACTCTGCGGTCTA
TTACTGTACTACGGGGTTTGCTTACTGGGGCCAAGGGACTCTGGTCACTGTCTCTG
CA

3D5 V$_K$ region:

GCCTCAGTCATAATGTCCAGAGGACAAATTGTTCTCACCCAGTCTCCAGCAATCATG
TCTGCATCTCTAGGGGAGGAGATCACCCTAACCTGCAGTGCCAGTTCGAGTATAAG
TTACATGCACTGGTACCAGCAGAAGTCAGGCACTTCTCCCAAACTCTTGATTTATAC
CACATCCACCCTGTCTTCTGGAGTCCCTTCTCGCTTCAGTGGCAGTGGGTCTGGGA
CCTTTTATTCTCTCACAATCAGCAGTGTGGAGGCTGAAGATGCTGCCGATTATTACT
GCCATCAGTCGAGTAGTTATCCGTATACATTCGGAGGGGGGACCAAGCTGGAAATA
AAACGGGCTGATGCT

4G5 V$_H$ region:

CAGGTCCAACTGCAGCAGTCTGGGGCTGAACTGGTGAAGCCTGGGACTTCAGTGAA
GTTGTCCTGCAAGGCTTCTGGCTACACCTTCACCAACTACTATATGTACTGGGTGAA
ACAGAGGCCTGGACAAGGCCTTGAGTGGATTGGAGAGATTAATACTAGAAATGGTG
GTAATAGGTTCAATGAGAAGTTCAAGAACAAGGCCATATTGACTGTAGACAAATCC
TCCAACACAGCATACATACAAGTCAGCAGCCTGACATCTGAGGACTCTGCGGTCTA
TTACTGTACTACGGGGTTTGCTTACTGGGGCCAAGGGACTCTGGTCACTGTCTCTG
CA

4G5 V$_K$ region:

GCCTCAGTCATAATGTCCAGAGGACAAATTGTTCTCACCCAGTCTCCAGCAATCATG
TCTGCATCTCTAGGGGAGGAGATCACCCTAACCTGCAGTGCCAGTTCGAGTATAAG
TTACATGCACTGGTACCAGCAGAAGTCAGGCACTTCTCCCAAACTCTTGATTTATAC
CACATCCACCCTGTCTTCTGGAGTCCCTTCTCGCTTCAGTGGCAGTGGGTCTGGGA
CCTTTTATTCTCTCACAATCAGCAGTGTGGAGGCTGAAGATGCTGCCGATTATTACT
GCCATCAGTCGAGTAGTCATCCGTATACATTCGGAGGGGGGACCAAGCTGGAAATA
AAACGGGCTGATGCT

FIG. 20

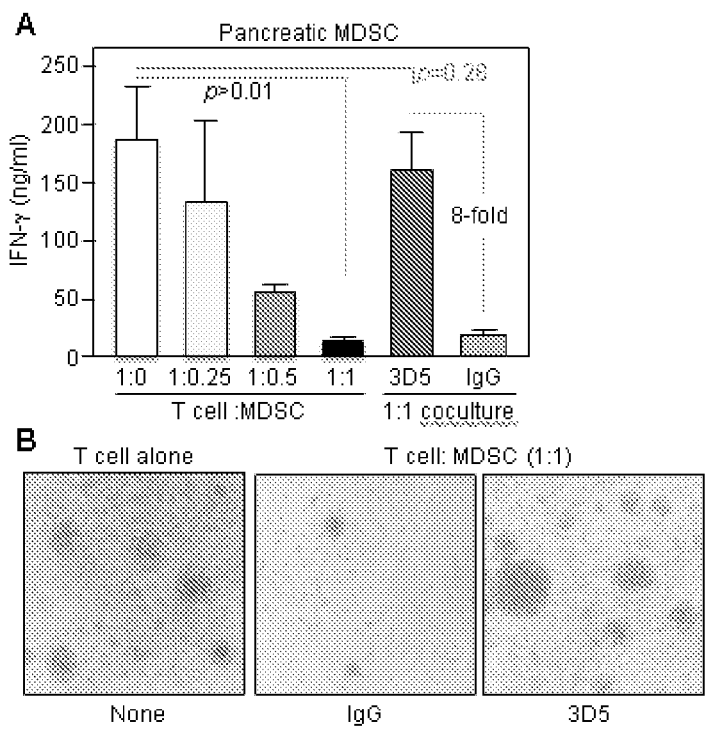
FIGS. 21A-B
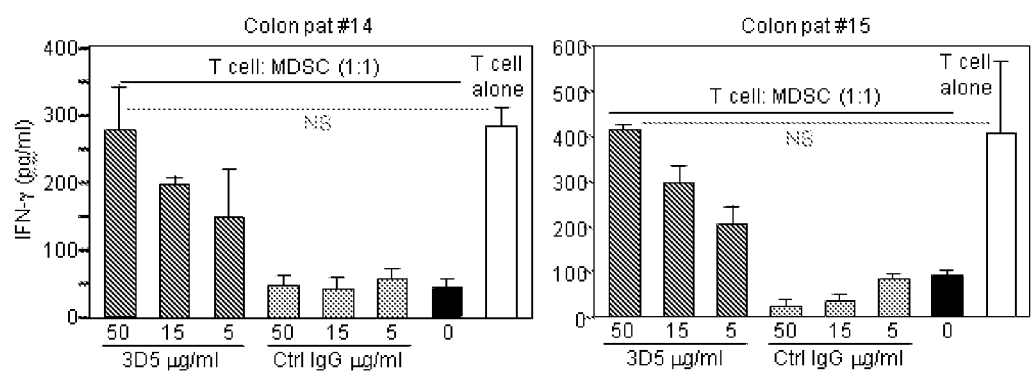
FIG. 22

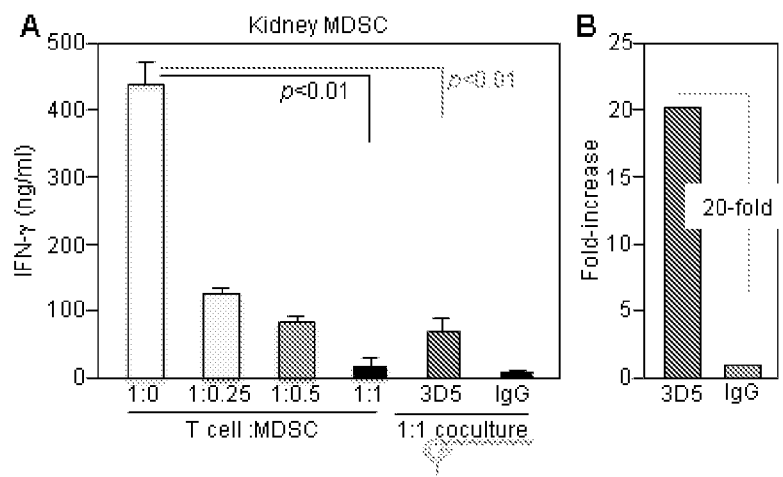
FIGS. 23A-B
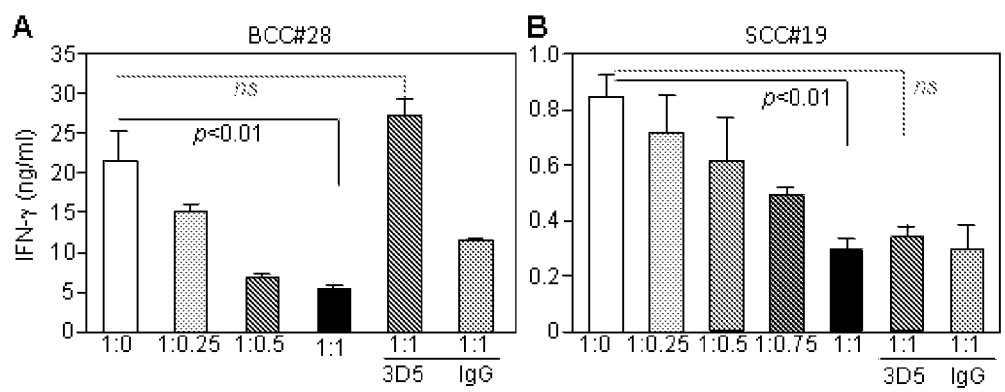
FIGS. 24A-B

| cancer | Total cases | %MDSC/PBMC | %DC HLA-/MDSC+ | %DC HLA-MDSC/PBMC |
|---|---|---|---|---|
| Healthy donors | 21 | 0.6%, 0.1-2.7 | 7.2%, 2.2-23 | 0.05%, 0.01-0.05 |
| Melanoma | 29 | 2.8%, 1.5-4.5 | 89%, 66-99 | 2.5%, 0.8-4.4 |
| BCC | 26 | 2.2%, 0.2-9.9 | 74%, 1.3-95 | 1.22%, 0.02-7.41 |
| SCC | 25 | 3.6%, 0.6-12.8 | 43%, 5.5-92 | 1.4%, 0.02-5.4 |
| Breast cancer | 10 | 1.5%, 0.5-5.9 | 91%, 59-98 | 1.3%, 0.5-5.5 |
| Colon cancer | 32 | 6.2%, 0.7-34 | 69%, 5.9-99 | 3.2%, 0.1-27 |
| Kidney cancer | 5 | 8.4%, 2.2-12 | 40%, 16-90 | 3.3%, 1.0-4.8 |
| Lung | 20 | 1.2%, 0.1-8.2 | 48%, 0.8-97 | 0.3%, 0-5.4 |
| Pancreatic cancer | 10 | 6%, 0.1-20 | 37%, 11-88 | 1.6%, 0.01-17 |
| Bile duct cancer | 2 | 2.3 and 32% | 70 and 98% | 12 and 2.2% |
| GEJ cancer** | 2 | 3.5 and 15% | 14 and 24% | 0.5 and 3.8% |
| Neuroendocrine tumor | 2 | 0.7 and 10% | 40 and 41% | 0.2 and 4.1% |
| Esophagus cancer | 1 | 6.1% | 17% | 1.0% |

FIG. 25

ANTI-DC-HIL ANTIBODIES FOR CANCER DIAGNOSIS, PROGNOSIS AND THERAPY

This application is a national phase application under 35 U.S.C. § 371 of International Application No. PCT/US2016/021472, filed Mar. 9, 2016, which claims benefit of priority to U.S. Provisional Application Ser. No. 62/131,473, filed Mar. 11, 2015, the entire contents of each of which are hereby incorporated by reference.

FEDERAL FUNDING CLAUSE

This invention was made with government support under grant number R01 AI064927-05, awarded by the National Institutes of Health. The government has certain rights in the invention

BACKGROUND

1. Field

The present disclosure relates generally to the fields of medicine, oncology, immunodiagnostics and cancer therapy.

2. Related Art

Skin cancer is the most common primary malignancy in humans, and melanoma is the type associated with highest mortality. Recent advances in the treatment of metastatic melanoma involve gene-targeted and immune-based modalities that have led to some improvement in patient survival. A barrier to optimal treatment is the ability of melanoma to counter anti-tumor T cell response by exploiting host-regulatory systems including regulatory T cells ($T_{reg}$), tumor-activated (or type 2) macrophages, immature dendritic cells (DC), and myeloid-derived suppressor cells (MDSCs) (Frey 2006; Diaz-Montero et al., 2009 and Serafini et al., 2006). Among these immune suppressors, MDSCs stand out because of their unsurpassed ability to inhibit T cell function.

MDSCs are distinguished by a CD11b+Gr-1+ phenotype in mice and consist of myeloid progenitor and immature myeloid cells. MDSC can be sorted into granulocytic and monocytic subtypes (Gabrilovich and Nagaraj, 2009 and Movahedi et al., 2008). Because the Gr-1 gene is not found in humans, CD14+HLA-DR$^{no/low}$ has been used to identify MDSCs in melanoma patients (Filipazzi et al., 2007). MDSCs in healthy individuals are not immunosuppressive, comprise 30% of BM cells, and differentiate into granulocytes, macrophages, or DC. By contrast, MDSCs in cancer patients are strongly immunosuppressive, proliferate exponentially, and their differentiation is blocked by tumor-derived soluble factors (Kusmartsev and Gabrilovich, 2003 and Gabrilovich et al., 1998). Thus, expansion of MDSC is an endogenous obstacle to successful cancer treatment.

MDSCs have been shown to suppress T cell and natural-killer cell functions (Liu et al., 2007), inhibit macrophage cytokine production (Sinha et al., 2007), and induce $T_{reg}$ (Serafini et al., 2008), either through suppressive soluble mediators like urea/L-ornithine (produced by arginase I) (Rodriguez et al., 2005 and Rodriguez and Ochoa, 2008), nitric oxide (NO) (Bingisser et al., 1998-Nagaraj et al., 2007), and ROS (Kusmartsev and Gabrilovich, 2003), or through coinhibitory pathways (Gabrilovich and Nagaraj, 2009) like CD80/CD86 on MDSC binding to CTLA-4 on T cells (Egen et al., 2002 and Yang et al., 2006) and PD-L1 on MDSCs binding to PD-1 on T cells (Liu et al., 2008 and Liu et al., 2008). Despite these findings, it is controversial which mechanism is critical to MDSCs suppressive function. This may be due to diversity on phenotype and even function of MDSCs population in mice and patients with different cancers. Thus, the exact signals responsible for the suppressive function are not fully understood.

APC's express the DC-HIL receptor (Shikano et al., 2001), also known as glycoprotein nmb (Weterman et al., 1995), osteoactivin (Safadi et al., 2001), and hematopoietic growth factor-inducible neurokinin-1 type (Metz et al., 2007). The inventors have previously demonstrated that DC-HIL on mouse and human APC binds to syndecan-4 (SD-4) on effector/memory (but not naive) T cells, and such binding inhibits T cell activation triggered by T cell receptors (TCR) (Chung et al., 2007 and Chung et al., 2009). The DC-HIL/SD-4 pathway curtails T cell-mediated inflammatory responses in mouse models of contact hypersensitivity and graft-versus-host disease (Chung et al., 2007 and Akiyoshi et al., 2010). Finally, mouse and human melanoma cells express DC-HIL on their surface that utilizes the SD-4 co-inhibitory pathway to suppress T cells for fostering melanoma growth (Tomihari et al., 2010). Thus, new reagents to impact the role DC-HIL plays in promoting tumor development and immune surveillance would be of great value.

SUMMARY

Thus, in accordance with the present disclosure, there is provided a method of predicting the progression of melanoma in a subject comprising:
   (a) obtaining a sample from said subject; and
   (b) determining in said sample:
      (i) a DC-HIL level on myeloid-derived suppressor cells (MDSCs) in said subject; or
      (ii) the number of DC-HIL-positive MDSCs;
wherein a higher level of DC-HIL on said MDSCs of step (b)(i) as compared to an MDSC from a non-cancer subject, or a higher number of DC-HIL-positive MDSCs in step (b)(ii), as compared to a non-cancer subject, indicates that said subject will have progression of melanoma. The method may involve performing steps (a) and (b) a second time and determining a change from the level or number from the previous assay. The sample may be a tumor biopsy, or blood or serum. Detection may comprise mass spectrometry, RT-PCR, or antibody detection, such as ELISA, RIA or Western blotting. The antibody may be characterized by CDR sequences as follows:

| CLONE | CDR1-L | CDR2-L | CDR3-L | CDR1-H | CDR2-H | CDR3-H |
|---|---|---|---|---|---|---|
| 3D5 | SSISY (SEQ ID NO: 1) | TTS (SEQ ID NO: 2) | HQSSSYPYT (SEQ ID NO: 3) | GYTFTNYY (SEQ ID NO: 4) | INTRNGGN (SEQ ID NO: 5) | TTGFAY (SEQ ID NO: 6) |
| 4G5 | SSISY (SEQ ID NO: 1) | TTS (SEQ ID NO: 2) | HQSSSHPYT (SEQ ID NO: 7) | GYTFTNYY (SEQ ID NO: 4) | INTRNGGN (SEQ ID NO: 5) | TTGFAY (SEQ ID NO: 6) |

The antibody may be a recombinant ScFv (single chain fragment variable) antibody, Fab fragment, F(ab')$_2$ fragment, or Fv fragment.

In another embodiment, there is provided a method of predicting the response of a subject to melanoma immunotherapy comprising:

(a) obtaining a sample from said subject; and
(b) determining in said sample:
  (i) a DC-HIL level on myeloid-derived suppressor cell (MDSCs) in said subject; or
  (ii) the number of DC-HIL-positive MDSCs;
wherein a lower level of DC-HIL on said MDSCs of step (b)(i) as compared to a level in a non-cancer subject, or a lower number of DC-HIL-positive MDSCs in step (b)(ii), as compared to a non-cancer subject, indicates that said subject will have a response to melanoma immunotherapy. The method may involve performing steps (a) and (b) a second time and determining a change from the level or number from the previous assay, wherein a lower level of DC-HIL on said MDSCs of step (b)(i) as compared to a previously measured level, or a lower number of DC-HIL-positive MDSCs in step (b)(ii), as compared to a previously measured number, indicates that said subject is responding to an intervening melanoma immunotherapy. The sample may be a tumor biopsy, or blood or serum. Detection may comprise mass spectrometry, RT-PCR, or antibody detection, such as ELISA, RIA or Western blotting. The antibody may be characterized by CDR sequences as follows:

| CLONE | CDR1-L | CDR2-L | CDR3-L | CDR1-H | CDR2-H | CDR3-H |
|---|---|---|---|---|---|---|
| 3D5 | SSISY (SEQ ID NO: 1) | TTS (SEQ ID NO: 2) | HQSSSYPYT (SEQ ID NO: 3) | GYTFTNYY (SEQ ID NO: 4) | INTRNGGN (SEQ ID NO: 5) | TTGFAY (SEQ ID NO: 6) |
| 4G5 | SSISY (SEQ ID NO: 1) | TTS (SEQ ID NO: 2) | HQSSSHPYT (SEQ ID NO: 7) | GYTFTNYY (SEQ ID NO: 4) | INTRNGGN (SEQ ID NO: 5) | TTGFAY (SEQ ID NO: 6) |

The antibody may be a recombinant ScFv (single chain fragment variable) antibody, Fab fragment, F(ab')$_2$ fragment, or Fv fragment.

In yet another embodiment, there is provided a monoclonal antibody or fragment thereof, wherein the antibody or fragment is characterized by CDR sequences as follows:

| CLONE | CDR1-L | CDR2-L | CDR3-L | CDR1-H | CDR2-H | CDR3-H |
|---|---|---|---|---|---|---|
| 3D5 | SSISY (SEQ ID NO: 1) | TTS (SEQ ID NO: 2) | HQSSSYPYT (SEQ ID NO: 3) | GYTFTNYY (SEQ ID NO: 4) | INTRNGGN (SEQ ID NO: 5) | TTGFAY (SEQ ID NO: 6) |
| 4G5 | SSISY (SEQ ID NO: 1) | TTS (SEQ ID NO: 2) | HQSSSHPYT (SEQ ID NO: 7) | GYTFTNYY (SEQ ID NO: 4) | INTRNGGN (SEQ ID NO: 5) | TTGFAY (SEQ ID NO: 6) |

The monoclonal antibody or antibody fragment may be encoded by a light chain variable sequence according to SEQ ID NOS: 8 or 10 a sequence having 70%, 80%, or 90% identity to SEQ ID NOS: 8 or 10, and a heavy variable chain sequence according to SEQ ID NOS: 9 or 11 or a sequence having 70%, 80% or 90% identity to SEQ ID NOS: 9 or 11, respectively. monoclonal antibody or antibody fragment may be encoded by a light chain variable sequence according to SEQ ID NOS: 8 or 10 a sequence having 95% identity to SEQ ID NOS: 8 or 10, and a heavy variable chain sequence according to SEQ ID NOS: 9 or 11 or a sequence having 95% identity to SEQ ID NOS: 9 or 10, respectively. The monoclonal antibody may comprise light and heavy chain variable region sequences comprising SEQ ID NO: 12 and SEQ ID NO: 13, or may comprise light and heavy chain variable region sequences comprising SEQ ID NO: 14 and 15, respectively. The monoclonal antibody or fragment may be a single chain antibody, a single domain antibody, a chimeric antibody, or a Fab fragment. The monoclonal antibody may be a recombinant antibody having specificity for DC-HIL and a second MDSC surface antigen. The monoclonal antibody or antibody fragment may be a murine antibody. The monoclonal antibody may be an IgG. The monoclonal antibody may be a humanized antibody. The monoclaon antibody may further comprise an antitumor drug linked thereto. The antitumor drug may be linked to said antibody through a photolabile linker, or through an enzymatically-cleaved linker. The antitumor drug may be a toxin, a radioisotope, a cytokine, or an enzyme. Also provided is a hybridoma expressing any of the monoclonal antibodies or fragments set forth above.

In yet another embodiment, there is provided a method of treating cancer comprising administering to said subject an antibody that binds to DC-HIL on the surface of a myeloid-derived suppressor cell (MDSC). The cancer may be melanoma. The cancer may be lung cancer, brain cancer, head & neck cancer, breast cancer, skin cancer, liver cancer, pancreatic cancer, stomach cancer, colon cancer, rectal cancer, uterine cancer, cervical cancer, ovarian cancer, testicular cancer, or esophageal cancer. The method may further comprise assessing the number of DC-HIL-positive MDSCs in said subject, and even further comprises assessing the level of DC-HIL on MDSCs from said subject. The method may also further comprise treating said subject with a second anti-cancer agent or treatment, such as chemotherapy, radiotherapy, immunotherapy, hormonal therapy, or toxin therapy. The second anti-cancer agent or treatment may be given at the same time as said antibody, or may be given before and/or after said antibody. The melanoma may be metastatic, multiply drug resistant or recurrent. The monoclonal antibody or fragment may be a single chain antibody, a single domain antibody, a chimeric antibody, or a Fab fragment. The monoclonal antibody may be a recombinant antibody having specificity for DC-HIL and a second MDSC surface antigen. The monoclonal antibody or antibody fragment may be a murine antibody. The monoclonal antibody may be an IgG. The monoclonal antibody may be a humanized antibody. The antibody may further comprise an antitumor drug linked thereto. The antitumor drug may be linked to said antibody through a photolabile linker, or through an enzymatically-cleaved linker. The antitumor drug may be a toxin, a radioisotope, a cytokine, or an enzyme. The antibody or fragment may be conjugated to a bead, a liposome or a nanoparticle, and such bead, liposome or nanoparticle comprises an antitumor drug. The antibody or antibody fragment is characterized by CDR sequences as follows:

| CLONE | CDR1-L | CDR2-L | CDR3-L | CDR1-H | CDR2-H | CDR3-H |
|---|---|---|---|---|---|---|
| 3D5 | SSISY (SEQ ID NO: 1) | TTS (SEQ ID NO: 2) | HQSSSYPYT (SEQ ID NO: 3) | GYTFTNYY (SEQ ID NO: 4) | INTRNGGN (SEQ ID NO: 5) | TTGFAY (SEQ ID NO: 6) |
| 4G5 | SSISY (SEQ ID NO: 1) | TTS (SEQ ID NO: 2) | HQSSSHPYT (SEQ ID NO: 7) | GYTFTNYY (SEQ ID NO: 4) | INTRNGGN (SEQ ID NO: 5) | TTGFAY (SEQ ID NO: 6) |

The monoclonal antibody or antibody fragment may be encoded by a light chain variable sequence according to SEQ ID NOS: 8 or 10 a sequence having 70%, 80%, or 90% identity to SEQ ID NOS: 8 or 10, and a heavy variable chain sequence according to SEQ ID NOS: 9 or 11 or a sequence having 70%, 80% or 90% identity to SEQ ID NOS: 9 or 11, respectively. monoclonal antibody or antibody fragment may be encoded by a light chain variable sequence according to SEQ ID NOS: 8 or 10 a sequence having 95% identity to SEQ ID NOS: 8 or 10, and a heavy variable chain sequence according to SEQ ID NOS: 9 or 11 or a sequence having 95% identity to SEQ ID NOS: 8 or 10, respectively. The monoclonal antibody may comprise light and heavy chain variable region sequences comprising SEQ ID NO: 12 and SEQ ID NO: 13, or may comprise light and heavy chain variable region sequences comprising SEQ ID NO: 14 and 15, respectively.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) WT allele (consisting of 11 exons) of C57BL/6 background and targeted KO allele are represented schematically. (FIG. 1B) Mouse DNA samples were PCR-amplified with 3 PCR primers (shown on the map): (1) intron between exons 1 and 2 (669 bp PCR band by primers #1 and #2); and (2) region spanning the intron to Neo gene (952 bp by primers #1 and #3), and separated on 1.5% agarose gel. WT and KO allele produces bands of 669 and 952 bp, respectively; heterozygote showed a mixed pattern. (FIG. 1C) Total RNA isolated from BM-derived DC of a KO or WT mouse was analyzed by RT-PCR using 2 primer sets to amplify exons 2-3 (E2-3, 416 bp) and exons 5-9 (E5-9, 673 bp). β-actin mRNA was also PCR-amplified. (FIG. 1D) BM-DC were used to immunoblot DC-HIL and b-actin proteins (20 mg of crude protein/lane) using 1E4 anti-DC-HIL and anti-b-actin Ab. Total proteins were also stained by Coomassie blue. (FIGS. 1E-F) BM-DC or macrophages (MF) from WT or KO mice were examined by FACS for expression of DC-HIL and CD11c (FIG. 1E) or CD11b (FIG. 1F). (FIG. 1G) Varying numbers of BM-DC from WT or KO mice were cocultured with $CD4^+$ or $CD8^+$ T cells (from OT-II or OT-I transgenic mice, respectively) with OVA peptide, and IL-2 and/or IFN-g secretion measured. (FIG. 1H) DC preparations were assayed for surface expression of CD80 and CD86 on $CD11c^+$ cells. Two other KO and WT mice showed similar results. *Students' t-test ($p<0.001$) between WT and KO.

(FIG. 2A) Tumor volume of B16 cells implanted into WT or DC-HIL KO mice (n=5). (FIG. 2B) Tumor volume after implanting DC-HIL-KD-B16 cells (n=5). Lung metastasis (FIG. 2C) at 19 days after B16 cells injected i.v. into WT or KO mice (n=10); lung weight, number of metastatic foci, melanin content/lung, and melanin content/focus plotted (FIG. 2D). Representative data from 3 separate experiments, *$p<0.01$ versus WT.

(FIG. 3A) Splenocytes from B16 melanoma-bearing or tumor-free mice (n=3) were assayed for % $DC-HIL^+$ cells in 3 myeloid populations. (FIGS. 3B-C) MDSC isolated from mice with (FIG. 3B) or without (FIG. 3C) melanoma were examined for expression of Gr1 and coinhibitory receptors (%). (FIG. 3D) These myeloid cells (increasing cell ratios) were cocultured with CFSE-labeled T-cells activated by anti-CD3/CD28 Ab. T-cell proliferation (%) was determined by FACS (histograms). (FIG. 3E) Purified myeloid cells were examined for T cell-stimulatory capacity. Different numbers of myeloid cells were pulsed with gp100 Ag and added to culture of $CD8^+$ pmel-1 T-cells. Culture of T-cells with Ag served as control (No). T-cell proliferation was measured by $^3$H-thymidine (TdR) incorporation. *$p<0.01$.

(FIG. 4A) BM cells were prepared from the femur, from which MDSC were purified and fluorescently stained with anti-Gr1 and anti-DC-HIL mAb (or control IgG). (FIG. 4B) Peripheral blood was collected from mouse tail veins. (FIG. 4C) Tumor-infiltrating cells were prepared from B16 tumor (~2 cm$^3$): The tumor was minced in PBS, treated with digestive enzymes, and applied to Ficoll-gradient to remove debris. % $DC-HIL^+$ cells among total MDSC cells are shown in dot-plots. (FIG. 4D) MDSC purified from splenocytes of mice with B16 melanoma were analyzed for expression of Gr-1 vs. Ly6C. Based on differential expression of these markers, MDSC sorted into 4 different fractions: Fr. 1 ($Ly6C^{high}Gr1^{low}$); Fr. 2 ($Ly6C^{med}Gr1^{hgih}$); Fr. 3 ($Ly6C^{med}Gr1^{low}$); and Fr. 4 ($Ly6C^{low}Gr1^{low}$). Each fraction was examined for DC-HIL expression: open and gray-filled histograms show anti-DC-HIL mAb and control IgG staining, respectively. Fr. 1 showed highest expression of DC-HIL. (FIG. 4E) MDSC subsets (Fr. 1 through Fr. 4) were purified by FACS sorting and cocultured with pmel-1 splenocytes/Ag at different cell ratios. T cell activation was assessed by proliferation, and the suppressive ability of each Fr or unfractionated MDSC is expressed as % suppression (1-cpm of MDSC-added culture/cpm of T cell alone×100%). *$p<0.001$ between Fr.1 and Fr.2. Data are representative of 3 experiments.

(FIGS. 5A-B) MDSC from melanoma-bearing mice were cocultured with pmel-1 splenocytes (Spl), gp100 Ag, and anti-DC-HIL mAb (FIG. 5A), anti-coinhibitor Ab or control IgG (FIG. 5B). $^3$H-TdR incorporation measured. (FIG. 5C) Undepleted ($DC-HIL^+$) or DC-HIL-depleted ($DC-HIL^{neg}$) MDSC were assayed for suppression of pmel-1 splenocyte proliferation triggered by Ag (increasing ratios).

(FIG. 5D) Mice (n=5) injected with pmel-1 CD8⁺ T-cells and DC-HIL⁺ MDSC or DC-HIL$^{neg}$ MDSC. Ten days after giving gp100, IFN-g-producing cells in LN were counted. (FIG. 5E) Tumor growth following coinjection of DC-HIL⁺ or DC-HIL$^{neg}$ MDSC with B16 cells s.c. into naive mice (n=5). Using similar methods, DC-HIL$^{-/-}$ MDSC were compared with DC-HIL$^{+/+}$ counterparts for DC-HIL expression by FACS (FIG. 5F), T-cell suppressing (FIG. 5G) and tumor-promoting ability (CD11b$^{neg}$ cells as control) (FIG. 5H). *p<0.01.

(FIGS. 7A-C) MDSC cocultured with pmel-1 splenocytes (1:1 ratio) with inhibitors; including (FIG. 7A) anti-cytokine Ab; (FIG. 7B) 5 mM L-N$^G$-monomethyl-arginine citrate (NOSs); 0.5 mM N$^6$-(1-iminoethyl)-L-lysine (NOS-2); 1 mM N-hydroxyl-nor-arginine (Arg); 0.2 mM 1-methyl-tryptophan (Indol); 1000 U/ml catalase (C-ROS); and 200 U/ml superoxide dismutase (S-ROS); and (FIG. 7C) anti-DC-HIL mAb or DC-HIL-Fc. ³H-TdR uptake was measured. (FIG. 7D) MDSC cocultured with SD-4$^{+/+}$ or SD-4$^{-/-}$ pmel-1 splenocytes. (FIGS. 7E-I) At varying times after crosslinking with Ab, MDSC were assayed for: tyrosine-phosphorylation (p-Tyr) on DC-HIL protein (FIG. 7E); cytokine mRNA and secretion (FIGS. 7F-G); mRNA of NOS genes (FIG. 7H); or NO production (FIG. 7I). Data (mean±sd, n=3) are shown as fold increase relative to control. *p<0.01.

(FIG. 8A) Tumor volume 6 days after implanting B16 cells into WT mice (n=7), mice injected with anti-DC-HIL mAb or control IgG on indicated days (closed arrows). On days shown by gray arrows in FIG. 8A, blood taken from mouse, MDSC counted from PBMCs by FACS (FIG. 8B), and data summarized (FIG. 8C). (FIG. 8D) A day after 3 injections, IFN-g-secreting cells in spleen or LN in each mouse (n=3) counted as number per 1×10⁴ cells. (FIG. 8E) Tumor volume on mice treated with the 2 Abs 11 days after implanting KD-B16 cells (n=7). (FIG. 8F) Tumor volume on DC-HIL$^{-/-}$ mice treated with Ab 7 days after co-injection of B16 and MDSC. *p<0.001.

(FIG. 11A) Specificity of 3D5 mAb to DC-HIL: protein or total cell extracts were subjected to SDS-PAGE/immunoblotting analysis with 1 mg/ml. DC-HIL-Fc (a recombinant protein consisting of the extracellular domain of DC-HIL fused to the Fc portion of Ig), mIgG (mouse IgG, a control for DC-HIL-Fc) and cell extracts from COS-1 cells transfected with a empty vector or DC-HIL gene, or from varying human cell lines (embryonal fibroblast 293T, melanoma SK-MEL-28, and primary cultured melanocytes). Closed and open arrow heads indicate DC-HIL proteins and non-specific bands, respectively. (FIG. 11B) Immunoblotting with 4G5 mAb. (FIG. 11C) SK-MEL-28 cells were stained with control IgG (shown in closed histograms), 3D5 or 4G5 mAb (10 mg/ml, open histograms) and analyzed for expression of surface-DC-HIL by FACS. MIF means mean fluorescence intensity.

(FIG. 12D) % blood DC-HIL⁺MDSCs/PBMCs was assayed at indicated times post-resection in 9 patients with stage 0 melanoma (data for patient M71 are in red). Detailed data are referred to FIGS. 14 and 15. *p<0.001 and **p<0.01. Note that DC-HIL expression was assayed using 3D5 anti-DC-HIL mAb.

FIG. 13. Melanoma patients and healthy controls used for study. The inventors recruited melanoma patients staged clinically based on American Joint Committee on Cancer criteria: metastasis to distant organ (stage IV); lymph node metastasis (stage III); limited to skin with varying thickness (stage 0-II). Patients with dysplastic nevi (atypical but not malignant histological changes) and healthy donors served as negative controls.

FIG. 14. Frequency of blood CD14⁺HLA-DR$^{no/low}$ MDSCs in melanoma patients after resection. All patients were diagnosed for melanoma in situ (MIS, stage 0). At indicated months after resection, PBMCs isolated from patients were analyzed for immunological features. "0 month" means time of resection. M71 patient was found to have a second MIS 3 months after resection of the first melanoma.

Figures 15, 16:
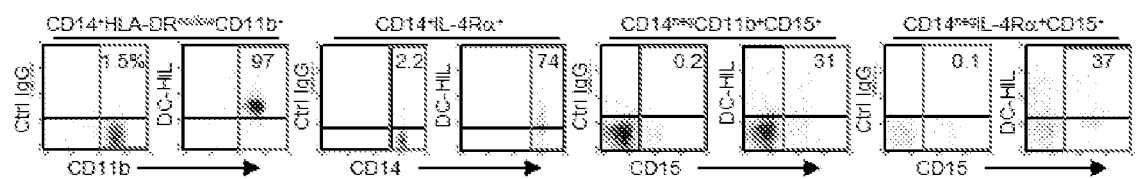

FIG. 15. Blood CD14$^+$HLA$^{no/low}$ MDSCs at sequential blood draws from healthy controls. Blood from healthy controls was drawn at indicated months and analyzed for immunological features.

FIG. 16. Expression of DC-HIL on four different MDSC subsets in melanoma patients. PBMCs isolated from a patient with melanoma of stage III were FACS analyzed for frequency of 4 different MDSC subsets (shown in red-lined box) and for DC-HIL expression: CD14$^+$HLA-DR$^{no/low}$CD11b$^+$ cells represent at 2.2% in total PBMCs with 97% DC-HIL$^+$ cells in the subset; CD14$^+$IL-4Ra$^+$ at 0.5% with 74% DC-HIL; CD14$^{neg}$CD11b$^+$CD15$^+$ at 0.2% with 31% DC-HIL; and CD14$^{neg}$IL-4Ra$^+$CD15$^+$ at 0.003% with 37% DC-HIL. Second melanoma patient showed similar results. Note that DC-HIL expression was measured using 3D5 anti-DC-HIL mAb.

FIGS. 17A-D. 3D5 anti-DC-HIL mAb treatment restored IFN-γ response of T-cells from melanoma patients. (FIG. 17A) CD14$^+$HLA-DR$^{no/low}$ MDSCs from a stage III patient or a healthy donor co-cultured with autologous T-cells/HLA-DR$^+$ cells (mixed with 1:1 ratio) at varying cell ratios with anti-CD2/CD3/CD28 Ab. After culturing for 5 days, IFN-γ secretion was measured (mean±sd, n=3). Representative data of 3 different patients. (FIG. 17B) Increasing doses of 3D5 mAb or control IgG were added to the coculture (1:1 cell ratio). (FIG. 17C) PBMCs from same patients with stages III/IV (n=25) were cultured for 5 days with 3D5 mAb or control IgG (20 mg/ml). IFN-γ amounts were assayed by ELISA, and fold increase by mAb vs. IgG is shown with Pearson's correlation coefficient r. (FIG. 17D) Same experiments were performed with all samples, and values of -fold increase in IFN-γ production plotted to cancer stage. *p<0.001.

FIG. 18. Effect of 4G5 anti-DC-HIL mAb on T cell-suppressive activity of MDSCs. CD14$^+$HLA-DR$^{neg}$ MDSCs were purified from a melanoma patient with Stage III and subjected to the T cell suppression assay shown in FIG. 17B, with a cell ratio of 1:1 (T cells: MDSCs) and 20 mg/ml of mIgG or 4G5 mAb. IFN-γ secretion was measured by ELISA. "ns' stands for not statistically significant.

Figure 19:
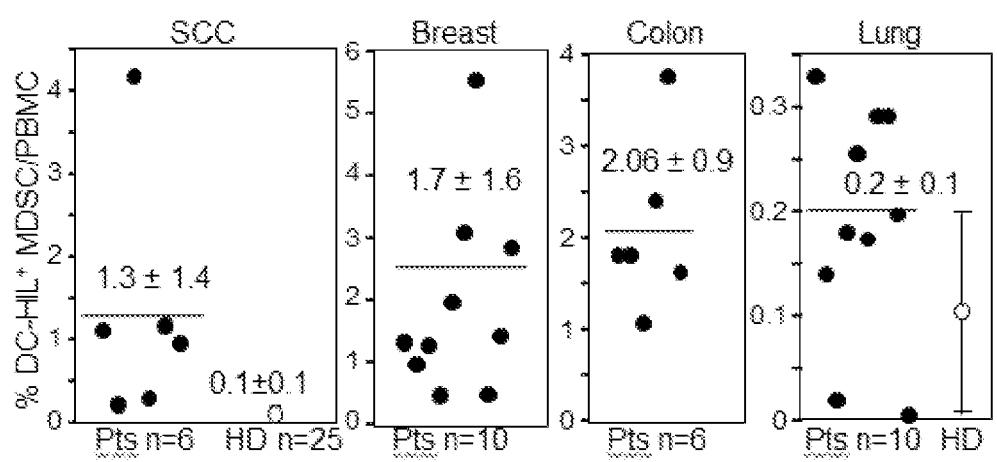

FIG. 19. Expansion of DC-HIL$^+$ MDSCs in blood of patients with non-melanoma cancers. CD14$^+$HLA-DR$^{no/low}$ MDSCs were determined for % in blood of patients with advanced cancers, including squamous cell carcinoma (SCC), breast cancer, colon or lung cancers, and plotted (mean±SD). Most lung cancers are non-small cell adenocarcinoma (9 out of 10). The range of healthy controls' values (HD, n=25) is shown in the graph. Note that DC-HIL expression was assayed using 3D5 anti-DC-HIL mAb.

FIG. 20. Nucleic acid sequences for variable regions. SEQ ID NOS: 12-15 are shown.

FIGS. 21A-B. T cell suppressor activity of MDSC isolated from pancreatic cancer patient. MDSC were purified from blood of a patient with metastatic pancreatic cancer: PBMCs were isolated from the blood, depleted of HLA-DR$^+$ cells, and sorted into CD14$^+$ and CD14$^{neg}$ fractions using Ab-coated magnetic beads: The former contains MDSC at 85-90% and the latter T cells at ~85%. (FIG. 21A) These cells were mixed at varying cell ratios with beads coated with anti-CD2/CD3/CD28 Ab (for activating T cells). 3D5 anti-DC-HIL mAb or control IgG (25 mg/ml) were added to some of 1:1 cocultures. After culturing for 5 days, IFN-g amounts in the culture supernatant were determined by ELISA (Data are shown by mean±SD, n=3). (FIG. 21B) On day 3 after culturing, culture of T cell alone and cocultures (1:1 cell ratio) with control IgG or 3D5 (25 mg/ml) were observed under microscope (10× magnification). Aggregates show T cell activation. Data shown are representative of T cell assays with MDSC from 4 different patients. Note that 3D5 mAb restored T cell response of pancreatic patients almost completely.

FIG. 22. T cell suppressor activity of MDSC from colon cancer patients. MDSC were purified from blood of patients (#14 and #15) with metastatic colon cancer (FIGS. 21A-B). T cells and MDSC from the same patient were mixed at a cell ratio of 1:1 with beads coated with anti-CD2/CD3/CD28 Ab. As control, T cell alone culture was set. Varying doses of 3D5 anti-DC-HIL mAb or control IgG were added to 1:1 cocultures: 0 means just 1:1 cocultures. Five days later, IFN-g amounts were assayed by ELISA (mean±SD, n=3). Data shown are representative of T cell assays with MDSC from 6 different patients. NS means "not significant" between 50 mg/ml 3D5 and T cell alone. Note that 3D5 mAb restored T cell response of colon patients almost completely.

FIGS. 23A-B. T cell suppressor activity of MDSC isolated from kidney cancer patient. MDSC were purified from blood of a patient with metastatic kidney cancer (FIGS. 21A-B). T cells and MDSC from the same patient were mixed at varying cell ratios with beads coated with anti-CD2/CD3/CD28 Ab. 3D5 anti-DC-HIL mAb or control IgG (25 mg/ml) were added to some of 1:1 cocultures. On day 5, IFN-g amounts in the culture supernatant were assayed by ELISA. Data shown are representative of T cell assays with MDSC from 2 different patients. Note that 3D5 mAb restored T cell response of kidney patients by 20-fold, compared to IgG-treated culture.

FIGS. 24A-B. T cell suppressor activity of MDSC isolated from BCC and SCC cancer patients. MDSC were purified from blood of a patient with skin cancer (basal cell carcinoma, BCC; or squamous cell carcinoma, SCC) as described in FIGS. 21A-B. T cells and MDSC from the same patient were mixed at varying cell ratios with beads coated with anti-CD2/CD3/CD28 Ab. 3D5 anti-DC-HIL mAb or control IgG (25 mg/ml) were added to some of 1:1 cocultures. After culturing for 5 days, IFN-g secretion was assayed by ELISA. Data shown are representative of T cell assays with MDSC from 2 different patients in each skin cancer. Note that 3D5 mAb restored T cell response of BCC patients completely, but no significant effect on SCC.

FIG. 25. DC-HIL$^+$MDSC blood levels in varying cancer types. Blood samples freshly isolated from varying cancer patients (n; total cases tested) were determined for % MDSC/PBMC, % DC-HIL+MDSC/total MDSC, and % DC-HIL+MDSC/PBMC. *Median and the range are shown. ** Gastro-esophageal junction.

DESCRIPTION OF ILLUSTRATIVE EMBODIMENTS

Here, the inventors report that DC-HIL is expressed markedly in macrophages, DC and MDSCs in mice bearing melanoma, but has little to no expression in tumor-free mice. Among those 3 myeloid cells, MDSCs were the most expanded and most potent in suppressing T cell activation, prompting them to probe a role for DC-HIL+MDSCs in melanoma growth. The inventors found DC-HIL to be the only co-inhibitory ligand, and IFN-γ and NO the only soluble mediators, required for MDSCs suppressor activity. Ligation of DC-HIL on MDSCs induced tyrosine phosphorylation of DC-HIL's intracellular domain, which then triggered the IFN-γ/NOS-2 pathway (Kamijo et al., 1994).

Deficient DC-HIL gene expression markedly reduced melanoma growth and metastasis in mice, and blocking DC-HIL function by anti-DC-HIL mAb infusion into melanoma-bearing mice inhibited tumor growth and prevented MDSC expansion. These beneficial outcomes resulted from negation of the suppressive function of DC-HIL+MDSCs (but not of DC-HIL+melanoma nor DC-HIL+APC).

The inventors also found DC-HIL to be induced in circulating MDSCs of metastatic melanoma patients, and that DC-HIL is required for MDSCs to suppress T cells. These results indicate that DC-HIL is the critical mediator of MDSCs deleterious effects in melanoma and that DC-HIL+ MDSCs can be targeted to improve melanoma immunotherapy. In furtherance of this hypothesis, the inventors have developed monoclonal antibodies against DC-HIL and found that they can restore activity of T-cells from cancer patients. These and other aspects of the disclosure are described in detail below.

I. MDSCs and DC-HIL

A. MDSCs

MDSCs (myeloid-derived suppressor cells) are a heterogenous population of immune cells from the myeloid lineage (a cluster of different cell types that originate from bone marrow stem cells), to which dendritic cells, macrophages and neutrophils also belong. However, MDSCs possess strong immunosuppressive activities rather than immunostimulatory properties. Myeloid cells interact with T cells (the effector immune cells that kill pathogens, infected and cancer cells) to regulate their functions, some of which are still under heated debate and close examination by the scientific community.

MDSCs are usually defined in mouse models as myeloid cells expressing high levels of CD11b and GR1, which exhibit potent T cell inhibitory activities. In human, MDSCs are generally defined as expressing high levels of some characteristic markers such as CD33, CD11b and low levels of HLA DR. However, it remains to be resolved as there is no international consensus on how human subsets of MDSCs should be defined.

Generally speaking, regardless of whether they are from mice or human, MDSCs suppressor function lies in their ability to inhibit T cell proliferation and activation. In healthy individuals, immature myeloid cells formed in the bone marrow differentiated to dendritic cells, macrophages and neutrophils. However, under chronic inflammatory conditions (viral and bacterial infections) or cancer, myeloid differentiation is skewed towards the expansion of MDSCs. These MDSCs infiltrate inflammation sites and tumors, where they stop immune responses by inhibiting T cells and NK cells, for example. MDSCs also accelerate angiogenesis, tumor progression and metastasis. Therefore, they have become a key therapeutic target. Clinical and experimental evidence has shown that cancer tissues with high infiltration of MDSC are associated with poor patient prognosis and resistance to therapies.

Cytokines are key signals involved in the generation of MDSCs. Tumor cell lines overexpressing colony stimulating factors (e.g., G-CSF and GM-CSF) have long been used in in vivo models of MDSC generation. GM-CSF, G-CSF and IL-6 allow the in vitro generation of MDSCs that retain their suppressive function in vivo. In addition to CSF, other cytokines such as IL-6, IL-10, VEGF, PGE2 and IL-1 have been implicated in the development and regulation of MDSCs. The myeloid-differentiation cytokine GM-CSF is a key factor in MDSC production from bone marrow, and it has been shown that the c/EBPβ transcription factor plays a key role in the generation of in vitro bone marrow-derived and in vivo tumor-induced MDSCs. Moreover, STAT3 promotes MDSC differentiation and expansion and IRF8 has been suggested to counterbalance MDSC-inducing signals.

MDSC activity was originally described as suppressors of T cells, in particular of CD8+ T-cell responses. The spectrum of action of MDSC activity also encompasses NK cells, dendritic cells and macrophages. Suppressor activity of MDSC is determined by their ability to inhibit the effector function of lymphocytes. Inhibition can be caused different mechanisms. It is primarily attributed to the effects of the metabolism of L-arginine. Another important factor influencing the activity of MDSCs is oppressive ROS.

In addition to host-derived factors, pharmacologic agents also have profound impact on MDSCs. Chemotherapeutic agents belonging to different classes have been reported to inhibit MDSCs. Although this effect may well be secondary to inhibition of hematopoietic progenitors, there may be grounds for search of selectivity based on long-known differential effects of these agents on immunocompetent cells and macrophages.

B. DC-HIL

Murine DC-HIL has a leader sequence (aa 1-19), a long extracellular domain (ECD, aa 20-499), a transmembrane domain (aa 500-523), and a cytoplasmic domain (aa 524-574). The ECD contains 11 potential N-glycosylation sites (NX(S/T)) and several putative O-glycosylation sites based on the stretch of proline-, serine-, and threonine-rich region, and a proline-rich region (aa 320-352) that presumably forms a hinge, as seen in proteins like IgA, which can mediate protein-protein interactions. Other functional motifs are an RGD sequence (aa 64-66), an integrin-binding sequence, and a KRFR (SEQ ID NO: 16) sequence (aa 23-26) that matches a heparin-binding motif composed of a stretch of basic residues (BBXB, where B represents a basic residue). The cytoplasmic tail contains an immunoreceptor tyrosine-based activation motif (ITAM (SEQ ID NO: 17), YXXI (SEQ ID NO: 18), aa 529-532, where X represents all other amino acid residues) and two lysosomal targeting di-leucine motifs (LL, aa 548-549 and 566-567).

Human DC-HIL has a leader sequence (aa 1-19), a long extracellular domain (ECD, aa 20-495), a transmembrane domain (aa 496-518), and a cytoplasmic domain (aa 519-572). The ECD contains 11 potential N-glycosylation sites (NX(S/T)) and several putative O-glycosylation sites based on the stretch of proline-, serine-, and threonine-rich region, and a proline-rich region (aa 320-349) that presumably forms a hinge, as seen in proteins like IgA, which can mediate protein-protein interactions. Other functional motifs are an RGD sequence (aa 64-66), an integrin-binding sequence, and a KRFH (SEQ ID NO: 19) sequence (aa 23-26) that matches a heparin-binding motif composed of a stretch of basic residues (BBXB, where B represents a basic residue). The cytoplasmic tail contains an immunoreceptor tyrosine-based activation motif (ITAM (SEQ ID NO: 17), YXYI (SEQ ID NO: 32), aa 525-528) and two lysosomal targeting di-leucine motifs (LL, aa 516-517 and 562-563).

Previously, the inventors identified DC-HIL as a highly glycosylated type I transmembrane protein of 125 and 95 kDa containing an extracellular Ig-like domain (Shikano et al., 2001). They also showed that DC-HIL is expressed constitutively at high levels on the surface of all dendritic cell subsets, including plasmacytoid dendritic cells and Langerhans cells and at lower levels on macrophages (Shikano et al., 2001), and that its expression can be induced in non-lymphoid cells (keratinocytes) following IFN-γ treatment. In human, DC-HIL is expressed constitutively at high levels by CD14+ monocytes and dendritic cells (but not by other leukocytes). They have also shown that DC-HIL is a negative regulator of T-cell activation (Chung et al., 2007a; Chung et al., 2007b) through binding to syndecan-4 on activated T-cells, indicating that interaction of DC-HIL with syndecan-4 attenuates T-cell activation triggered by anti-CD3 Ab or by APCs in a manner resembling the inhibitory function of PD-L1/PD-L2.

II. Producing Monoclonal Antibodies

A. General Methods

It will be understood that monoclonal antibodies binding to DC-HIL will have several applications. These include the production of diagnostic kits for use in detecting and diagnosing cancer, as well as for cancer immunosuppression and cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this disclosure were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, which in this case is for DC-HIL on the surface of MDSCs. Those of skill in the art, by assessing the binding specificity/affinity of a given antibody using techniques well known to those of skill in the art, can determine whether such antibodies fall within the scope of the instant claims. In one aspect, there is provided a monoclonal antibody having CDRs as defined below:

| CLONE | CDR1-L | CDR2-L | CDR3-L | CDR1-H | CDR2-H | CDR3-H |
|---|---|---|---|---|---|---|
| 3D5 | SSISY (SEQ ID NO: 1) | TTS (SEQ ID NO: 2) | HQSSSYPYT (SEQ ID NO: 3) | GYTFTNYY (SEQ ID NO: 4) | INTRNGGN (SEQ ID NO: 5) | TTGFAY (SEQ ID NO: 6) |
| 4G5 | SSISY (SEQ ID NO: 1) | TTS (SEQ ID NO: 2) | HQSSSHPYT (SEQ ID NO: 7) | GYTFTNYY (SEQ ID NO: 4) | INTRNGGN (SEQ ID NO: 5) | TTGFAY (SEQ ID NO: 6) |

Such antibodies may be produced by the clones discussed below in the Examples section using methods described herein.

In a second aspect, the antibodies may be defined by their variable sequence, which include additional "framework" regions. These are provided in SEQ ID NOS: 8-11 (protein) and SEQ ID NOS: 12-15 (nucleic acids). Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing apply to the nucleic acid sequences set forth as SEQ ID NOS: 12-15, and the amino acid sequences of SEQ ID NOS: 8-11.

C. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR products can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into a Lonza pConIgG1 or pConK2 plasmid vector, transfected into 293 Freestyle cells or Lonza CHO cells, and antibodies were collected and purified from the CHO cell supernatant. The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but nonimmunogenic portion (i.e., chimeric antibodies). PCT Application PCT/US86/02269; EP Application 184,187; EP Application 171,496; EP Application 173,494; PCT Application WO 20 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution.

Jones et al. (1986); Verhoeyen et al. (1988); Beidler et al. (1988); all of which are incorporated herein by reference. In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG4 can reduce immune effector functions associated with other isotypes. Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide.

Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C-terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, heterobifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak and Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibodyconjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques. In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.). Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Pharmaceutical Formulations and Treatment of Cancer

A. Cancers

Cancer results from the outgrowth of a clonal population of cells from tissue. The development of cancer, referred to as carcinogenesis. Unlike many antibody therapies for cancer, the antibodies of the present disclosure are directed instead to the DC-HIL molecules found on the surface of myeloid-derived suppressor cells (MDSCs).

Cancer cells to which the methods of the present disclosure can be applied include generally any cancer that is subject to the influence of MDSCs. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present disclosure may be particularly applied to such cancers so as to render them resectable, to prolong or re-induce remission, to prevent or limit metastasis, and/or to treat multi-drug resistant cancers.

B. Formulation and Administration

The present disclosure provides pharmaceutical compositions comprising anti-DC-HIL antibodies. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

C. Combination Therapies

It may also be desirable to provide combination treatments using antibodies of the present disclosure in conjunction with other therapeutic modalities. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent/therapy.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-DC-HIL antibody or the other therapy will be desired. Various combinations may be employed, where the antibody is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. To kill cells, inhibit cell growth, inhibit metastasis, inhibit angiogenesis or otherwise reverse or reduce the malignant phenotype of tumor cells, using the methods and compositions of the present disclosure, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

The antibodies of the disclosure may be particularly in enhancing the efficacy of cancer immunotherapies and vaccinations, anti-CTLA-4 therapy, anti-PD-1 therapy, or radiation therapy.

D. Non-Antibody Cancer Therapies

As an adjunct to the diagnostic aspects of the present disclosure, it may be desirable to make a treatment decision based on the outcome of a diagnostic method described herein, or to effect such a treatment. Treatment options are well known to those of skill in the art, and may include the DC-HIL antibodies of the disclosure, as well as co-therapies. These are discussed above. However, it may also prove appropriate to treat patients with other "standard" therapies where DC-HIL is not a relevant target. Again, in such situations, the goal may be to kill cells, inhibit cell growth, inhibit metastasis, inhibit angiogenesis or otherwise reverse or reduce the malignant phenotype of tumor cells. Agents or factors suitable for cancer therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," may be used. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with the present disclosure. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene. Chemotherapeutic agents contemplated to be of use, include, e.g., camptothecin, actinomycin-D, or mitomycin C. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m2 at 21 day intervals for doxorubicin, to 35-50 mg/m2 for etoposide intravenously or double the intravenous dose orally.

Microtubule inhibitors, such as taxanes, also are contemplated. These molecules are diterpenes produced by the plants of the genus Taxus, and include paclitaxel and docetaxel. Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in cancer therapy in accordance with the present disclosure.

Another possible therapy is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, it also is contemplated that immunotherapy, hormone therapy, toxin therapy and surgery can be used. It also should be pointed out that any of the foregoing therapies may prove useful by themselves in treating cancer. The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. Antibody Reagents/Conjugates

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Such molecules are optionally attached via cleavable linkers designed to allow the molecules to be released at or near the target site. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and U.S. Pat. No. 4,472,509). The imaging moieties used can be paramagnetic ions, radioactive isotopes, fluorochromes, NMR-detectable substances, and X-ray imaging agents. In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and described, for example, in U.S. Pat. Nos. 3,817,837, 3,850,752, 3,939,350, 3,996,345, 4,277, 437, 4,275,149 and U.S. Pat. No. 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. No. 4,472,509 and U.S. Pat. No. 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-phydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, there are immunodetection methods for binding, purifying, removing, quantifying and otherwise generally detecting DC-HIL and its associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of DC-HIL antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987).

In general, the immunobinding methods include obtaining a sample and contacting the sample with a first antibody in accordance with embodiments discussed herein, as the case may be, under conditions effective to allow the formation of immunocomplexes. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to DC-HIL present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and U.S. Pat. No. 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the DC-HIL is added to the wells. After binding and washing to remove non-specifically bound immune complexes, the bound antigen may be detected.

Detection may be achieved by the addition of another anti-DC-HIL antibody that is linked to a detectable label. This type of ELISA is a simple "sandwich ELISA." Detection may also be achieved by the addition of a second anti-DC-HIL antibody, followed by the addition of a third antibody that has binding affinity for the second antibody, with the third antibody being linked to a detectable label.

In another exemplary ELISA, the samples suspected of containing the DC-HIL antigen are immobilized onto the well surface and then contacted with anti-DC-HIL antibody. After binding and washing to remove non-specifically bound immune complexes, the bound anti-DC-HIL antibodies are detected. Where the initial anti-DC-HIL antibodies are linked to a detectable label, the immune complexes may be detected directly. Again, the immune complexes may be detected using a second antibody that has binding affinity for the first anti-DC-HIL antibody, with the second antibody being linked to a detectable label.

Irrespective of the format employed, ELISAs have certain features in common, such as coating, incubating and binding, washing to remove non-specifically bound species, and detecting the bound immune complexes. These are described below. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween). After incubation with the labeled antibody, and subsequent to washing to remove unbound material, the amount of label is quantified, e.g., by incubation with a chromogenic 5 substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies may also be used in conjunction with both fresh-frozen and/or formalinfixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings. Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, there are immunodetection kits for use with the immunodetection methods described above. The immunodetection kits will thus comprise, in suitable container means, a first antibody that binds to DC-HIL antigen, and optionally an immunodetection reagent.

In certain embodiments, the DC-HIL antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the DC-HIL antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VI. Examples

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials And Methods

Reagents.

Ab against CD3 (145-2C11), CD11b (M1/70), CD11c (N418), CD14 (61D3), CD19 (eBio1D3), CD28 (37,51), CD80 (16A-10A1), CD86 (GL1), Gr-1 (RB6-8C5), HLA-DR (LN3), IFN-γ (XMG1.2), IL-10 (JES5-16E3), PD-L1 (MIH5), TGF-β1 (9016), Thy1.1 (HIS51) and control Ab were purchased from eBioscience; anti-phosphotyrosine (4G10) from Upstate Biotechnology; and all recombinant cytokines from Pepro Tech. The inventors generated 1E4 rat anti-mouse DC-HIL and UTX103 rabbit anti-mouse DC-HIL as described previously (Chung et al., 2009). DC-HIL-Fc fusion protein was produced by COS-1 cells and purified (Chung et al., 2007). The chemical inhibitors, L-NG-monomethyl-arginine citrate, N6-(1-iminoethyl)-L-lysine, N-hydroxyl-nor-arginine, 1-methyl-tryptophan, and catalase and superoxide dismutase, were purchased from Sigma-Aldrich. hgp100 peptide (KVPRNQDWL), OVA257-264 H-2Kb-class I (SIINFEKL), and OVA323-339 H-2Kb-class II peptide (ISQAVHAAHAEINEAGR) were synthesized by the Protein Chemistry Technology Center at UT Southwestern.

Animals and Cell Culture.

Female C57BL/6 mice and pmel-1 TCR transgenic mice (B6.Cg-Thy1a/CyTg(TcraTcrb)8Rest/J) (5- to 8-wk-old) were purchased from Harlan Breeders and Jackson Laboratory, respectively. The inventors generated DC-HIL gene-disrupted C57BL/6 mice: The left arm (5.1 Kb) and right arm (3.1 Kb) were isolated from a mouse chromosome BAC clone (from C57BL/6 mice) and inserted into the 5'-end and 3'-end, respectively, of the neo gene in pVPTK01 targeting vector. This vector was linearized by digestion of restriction enzyme I-CeuI (New England Biolabs) and electroporated into C57BL/6-derived embryonic stem cells (inGenious targeting laboratories). The targeted DC-HIL mutation-bearing ES cells were screened by differential sensitivity to G418 and TK and Southern blotting of genome DNA. Chimeric mice were produced by microinjection of blastocysts and backcrossed with C57BL/6 for 6 generations, and KO mice produced by breeding heterozygotes. SD-4-deficient mice (C57BL/6 genetic background) were obtained from by Dr. Kojima (Nagoya University) (Ishiguro et al., 2000). Control groups included mice with WT genotype (DC-HIL$^{+/+}$ or SD-4$^{+/+}$) from the same generation of backcross. SD-4-deficient pmel-1 mice were produced by breeding SD-4-deficient mice and pmel-1 transgenic mice. Following NIH guidelines, animals were housed in the pathogen-free facility of the Institutional Animal Care Use Center of The University of Texas Southwestern Medical Center. All animal protocols were approved by the Center. B16F10 (B16) melanoma cells were purchased from the American Type Culture Collection and maintained in DMEM supplemented with 10% FCS. KD-B16 melanoma cells were generated (28). Freshly isolated leukocytes were cultured in 10% FCS-RPMI 1640.

Preparation of Leukocytes.

For MDSC, B16F10 melanoma cells ($5 \times 10^5$) were harvested by treatment with 5% EDTA/trypsin, washed, resuspended in 50 µl of DPBS, and then injected s.c. into the right shaved flank of WT or KO mice (3-10 mice per experiment). Three weeks later, spleen cells were pooled from mice, depleted of CD11c+ and CD19+ cells using 10 µl of anti-biotin-beads (Invitrogen) coated with corresponding Ab, incubated with anti-CD11b Ab-coated magnetic beads (Miltenyi Biotec), and then applied to a magnetic column. Eluate is the CD11b+ cell fraction (MDSC preparation) and the pass through is the CD11 b$^{neg}$ fraction (control cells for MDSC). Normally, MDSC preparations contain ~95% CD11b+Gr-1+ cells. MDSC were also isolated from BM and peripheral blood using the same method. Tumor-infiltrating cells were prepared from B16 tumor (~2 cm$^3$): The tumor was minced in PBS, treated with digestive enzyme mixture [0.5 mg/ml Collagenase I and IV and 0.1 mg/ml DNase I (Sigma-Aldrich)] at 37° C. for 1 h, and applied to Ficoll-gradient to remove cell debris. BM-DC were harvested from day 6 culture of BM cells isolated from C57BL/6 mice (Chung et al., 2009). Macrophages and DC were also purified from spleen cells prepared from mice bearing B16 tumor (3 weeks after tumor inoculation) by FACS sorting of F4/80+ and CD11c+ cells, respectively. These preparations contain ~95% of macrophage and DC, respectively.

Flow Cytometry (FACS).

Leukocytes ($1-5 \times 10^5$ cells) were incubated with primary mAb or the isotypic control IgG (each 1-10 µg/ml), and labeled with fluorescent secondary Ab (1 µg/ml). Fluorescence intensity of stained cells was analyzed by FACSCalibur (BD Biosciences).

Ag Presentation Assay.

BM-DC prepared from BM cells of KO or WT mice were seeded on 96 well-plate ($1-20 \times 10^3$ cells/well), and pulsed for 3 hr with OVA peptide (2 µg/ml). Then, CD4+ or CD8+ T cells ($1 \times 10^5$/well) from OT-I or OT-II transgenic mice, respectively were added to the culture. One day after coculture, IL-2 and/or IFN-γ in the culture supernatant were measured by ELISA. To assay the T cell-stimulatory capacity of myeloid cells isolated from mice with B16 tumor, purified DC, macrophages or MDSC (increasing cell ratios to T cell) were added to pmel-1 spleen cells ($1 \times 10^5$ cells/well) with 1 µg/ml hgp100 peptide. After culturing for 2 d, proliferative response was measured by $^3$H-thymidine (1 µCi/well) incorporation with pulsing in the last 20 h of the culture period. Net cpm in T cells is calculated by subtracting background cpm in culture of myeloid cell alone plus peptide from cpm in the coculture.

T Cell Suppression Assay.

MDSC were purified from spleen cells of mice with B16 tumor and cocultured with pmel-1 spleen cells ($2 \times 10^5$/well) at varying cell ratios in the presence of 1 µg/ml hgp100 peptide for 3 d. T cell activation was measured by $^3$H-thymidine incorporation. For inhibition studies, inhibitors (varying doses of Ab or chemicals) were added separately to culture of spleen cells/MDSC (1:1 cell ratio). To examine impact of DC-HIL deletion on the suppressor activity, increasing doses of MDSC purified from WT or DC-HIL KO mice bearing B16 tumor were cocultured with pmel-1 spleen cells ($2 \times 10^5$/well). Alternatively, purified MDSC were depleted of DC-HIL+ cells using 10 µl of anti-biotin-beads (Invitrogen) precoated with anti-DC-HIL mAb (or IgG as control). To examine impact of SD-4 deletion on T cell susceptibility to MDSC function, spleen cells ($2 \times 10^5$/well) from SD-4+/+ or SD-4−/− pmel-1 transgenic mice were cocultured with 0.1 µg/ml hgp100 peptide and varying numbers of melanoma-MDSC.

To assay the ability of MDSC to suppress in vivo T cell response, day 0 WT mice (n=5) were i.v. injected with pmel-1 CD8+ T cells ($1 \times 10^7$ cells/mouse); day 3 they were also given i.v. injection of IgG-treated or DC-HIL-depleted MDSC and vaccinated with complete Freund's adjuvant plus gp100 peptide (1 mg/ml); and day 13 draining inguinal LN were procured from all mice and cultured for 2 d in Ab-coated wells with gp100 peptide (1 µg/ml). Cells secreting IFN-γ were counted by ELISPOT assay (eBiosciences).

Tyrosine Phosphorylation Assay.

Purified MDSC ($5 \times 10^6$ cells) were treated with UTX103 mAb or control rabbit IgG (10 µg/ml) on ice for 30 min, followed by crosslinking with 100 µg/ml goat anti-rabbit IgG. At indicated time periods at 37° C., treated MDSC were lysed using 500 µl of 2× lysis buffer (Chung et al., 2009). DC-HIL protein was immunoprecipitated by incubation at 4° C. for 3 h with 2-5 µg of UTX103 mAb and 2 h incubation with protein-A agarose (50 µl of 50% slurry). Immune complexes were then analyzed for expression of phospho-tyrosine by immunoblotting using biotinylated anti-phosphotyrosine (0.5 µg/ml) and HRP-streptavidin (1/10,000 dilution) (Chung et al., 2009). Blotted membranes were stripped and reanalyzed using 1E4 rat anti-DC-HIL mAb (1 µg/ml) and HRP-anti-rat IgG (1/10,000 dilution). Image acquisition and analysis of Ab-reactive bands were performed using ImageQuant 400 (Amersham Biosciences).

Tumor Growth and Metastasis Assays.

B16 cells ($5 \times 10^5$) were injected s.c. into the right flank of WT or DC-HIL KO mice (n=9). Tumor growth was monitored every other day by measuring perpendicular diameters using a metric caliper, and tumor volume estimated (Kamijo et al., 1994). To examine the ability of MDSC to promote tumor growth, MDSC (2×10⁶) purified from melanoma-bearing KO or WT mice (n=10) were mixed with 2×10⁵ B16 cells in a total volume of 50 μl DPBS, and then injected s.c. into naive WT mice (n=5). A week later, mice were i.v. injected again with purified MDSC (2×10⁶ cells/mouse). Control mice were injected with B16F10 cells alone. Tumor volume was monitored.

For lung metastasis, B16 cells (1×10⁶ cells) were harvested, resuspended in 200 μl of DPBS, and injected into WT or DC-HIL KO mice (n=10) via the lateral tail veil. Lungs were harvested 18 or 19 d post-injection, and their total weight, number of metastatic foci, and melanin content were determined (Tomihari et al., 2010).

Assays for Soluble Factors.

Melanoma-MDSC were cultured in 96-well plates (2×10⁵ cells/well, in triplicate) precoated with UTX103 mAb or control IgG (10 μg/ml). After 1 or 2 d of culture at 37° C., the culture supernatant and cell pellets were collected separately: the former tested cytokine secretion (IFN-γ, TNF-α, IL-10, and TGF-β1 using ELISA; and the latter tested whole cell extracts (to measure NO production using Griess method (De Santo et al., 2005)) or total RNA (to measure IFN-γ and NOS mRNA using quantitative PCR). The inventors also measured soluble factors in MDSC purified from spleen of WT or KO mice (n=5) with B16 tumor, which included NO, arginase activity (assayed by a chromogen that measures urea produced by the enzyme) (Rodriguez et al., 2005), and ROS by DCFH-DA fluorescent dye (Kim et al., 2010).

Quantitative PCR.

IFN-γ and NOS mRNA expression in total RNA samples was assayed by quantitative PCR following the manufacturer's recommendations (LightCycler FastStart DNA Masterplus SYBR Green I, Roche). Primers for IFN-γ, 5'-AGTGGAGCAGGTGAAGAGTG-3' (SEQ ID NO: 24) and 5'-TTCGGAGAGAGGTACAAACG-3' (SEQ ID NO: 25), for NOS-1, 5'-TGTGCTTTGATGGAGATGAGG-3' (SEQ ID NO: 26) and 5'-CAAAGTTGTCTCTGAG-GTCTGG-3' (SEQ ID NO: 27), for NOS-2 are 5'-AGAGT-GAAAAGTCCAGCCG-3' (SEQ ID NO: 28) and 5'-ACAACTCGCTCCAAGATTCC-3' (SEQ ID NO: 29), and for NOS-3 are 5'-CTGCCACCTGATCCTAACTTG-3' (SEQ ID NO: 30) and 5'-CAGCCAAACACCAAAGT-CATG-3' (SEQ ID NO: 31). PCR amplification efficiencies were determined for each gene prior to the relative quantification and were similar for the target gene and the endogenous control (GAPDH). mRNA expression for each sample was expressed as the expression level relative to GAPDH gene, which was quantitated using the comparative Ct method and the formula 2-ΔΔCT.

Ab Treatment of Mice.

On day 0, C57BL/6 (14 mice) were inoculated s.c. with 5×10⁵ B16 or KD-B16 cells (Tomihari et al., 2010). On day 6 (for mice bearing B16F10 tumor) or day 11 (for KD-B16 tumor), mice were sorted to 2 groups with similar average tumor volume (~0.1 cm3) and i.p. injected with UTX103 mAb or rabbit IgG (200 μg/mouse) every other day for a total of 5-6 injections.

To examine the effect of UTX103 mAb on T cell-stimulatory capacity of DC, DC-HIL⁻/⁻ mice (12 mice) were implanted s.c. with 5×10⁵ B16 cells, and 2 weeks later mice were sorted into 3 groups (n=4) with similar average tumor volume (~0.2 cm³). The same day (day 0), the mice were i.v. injected with 1×10⁷ CFSE-labeled pmel-1 T cells and immediately afterwards i.v. injected with 5×10⁶ BM-DC unpulsed or pulsed for 2 h with the corresponding Ag (1 μg/ml). On days 0 and 2, UTX103 mAb or control IgG (200 μg/mouse) was injected i.p. into treated mice. On day 3, spleen and draining LN were procured and assayed for CFSE fluorescence intensity of Thy1.1+ cells by FACS.

Circulating MDSC.

At indicated time points before or after Ab injection into mice bearing melanoma, 5 representative mice for each group were chosen; blood samples (50-100 μl) were taken from mouse tails, depleted of red blood cells by lysis, pulsed with OVA257-264 peptide (1 μg/ml), and stained with PE anti-OVA-H-2Kb (to count nucleated cells), APC anti-CD11b, and FITC anti-Gr-1 for FACS analysis. H-2Kb+ cells were gated and examined for % of CD11b+Gr-1+ MDSC.

Melanoma Patients and Controls.

The study was approved by The University of Texas Southwestern Medical Center Institutional Review Board and was conducted according to principles of the Declaration of Helsinki. Participants gave written informed consent in accordance with the Declaration of Helsinki. Blood samples were taken from 6 healthy donors and 6 melanoma patients. All patients were classified as stage III metastatic melanoma (American Joint Committee on Cancer criteria) and had been treated previously with immunotherapy. Six patients had a median age of 53 years and included 4 women and 2 men.

Human MDSC and T Cell Assay.

PBMCs (5×10⁵ cells/reaction) isolated using cell preparation tube with sodium citrate (BD Vacutainer CPT, BD Biosciences) were treated with human IgG and incubated with 10 μg/ml 3D5 anti-human DC-HIL mAb (or control IgG) and 1 μg/ml PE-anti-mouse IgG [F(ab')2 fragment]. After washing, cells were further stained with APC anti-HLA-DR and FITC anti-CD14 Ab (each 10 μg/ml), and analyzed by FACS.

CD14+HLA-DR$^{no/low}$ MDSC, HLA-DR+ cells, and T cells were freshly isolated from blood samples of same donor: PBMCs from a melanoma patient (or healthy donors) were fractionated into HLA-DR$^{neg}$ and HLA-DR+ cells (control) using magnetic beads (Miltenyi Biotec). The former fraction was incubated with anti-CD14 Ab-coated magnetic beads (Miltenyi), and then applied to a column. The column eluate (the MDSC fraction containing >95% of CD14+HLA-DR$^{no/low}$ cells), and the pass-through fraction was used for isolation of T cells using Pan-T cell isolation kit (Miltenyi). MDSC or HLA-DR+ control cells were cocultured with autologous T cells (1×10⁵ cells/well) at varying cell ratios in the presence of anti-CD2/CD3/CD28 beads (Miltenyi) (1.5 beads per T cell) in 96 microculture wells (triplicate) for 5 d. For inhibition studies, varying doses of 3D5 mAb or control IgG were added to the same culture (1:1 cell ratio). IFN-γ production was determined by ELISA, and suppressive activity of MDSC was assessed by IFN-γ amount (%) relative to that of control culture (corresponding HLA-DR+/T cell culture).

Statistical Analysis.

Statistical analyses were performed using student's t test. In all cases, p values were calculated using two-sided t test, with p (<0.01) considered significant. All data shown are representative of at least 2 independent experiments.

Example 2—Results

DC-HIL Gene Disruption Enhances the T Cell-Stimulatory Capacity of DC.

To study the in vivo significance of the DC-HIL receptor on APC, the inventors created DC-HIL gene-knocked out (KO) mice by replacing a fragment spanning exons 2-4 with a targeting vector (FIG. 1A) to produce a frame-shift replacement in downstream exons caused by mismatched acceptor-donor sites for RNA splicing between exons 1 and 5. The targeted DC-HIL mutation was introduced into C57BL/6 mice, and the KO allele confirmed by PCR analysis of genomic DNA (FIG. 1B).

Figure 1:
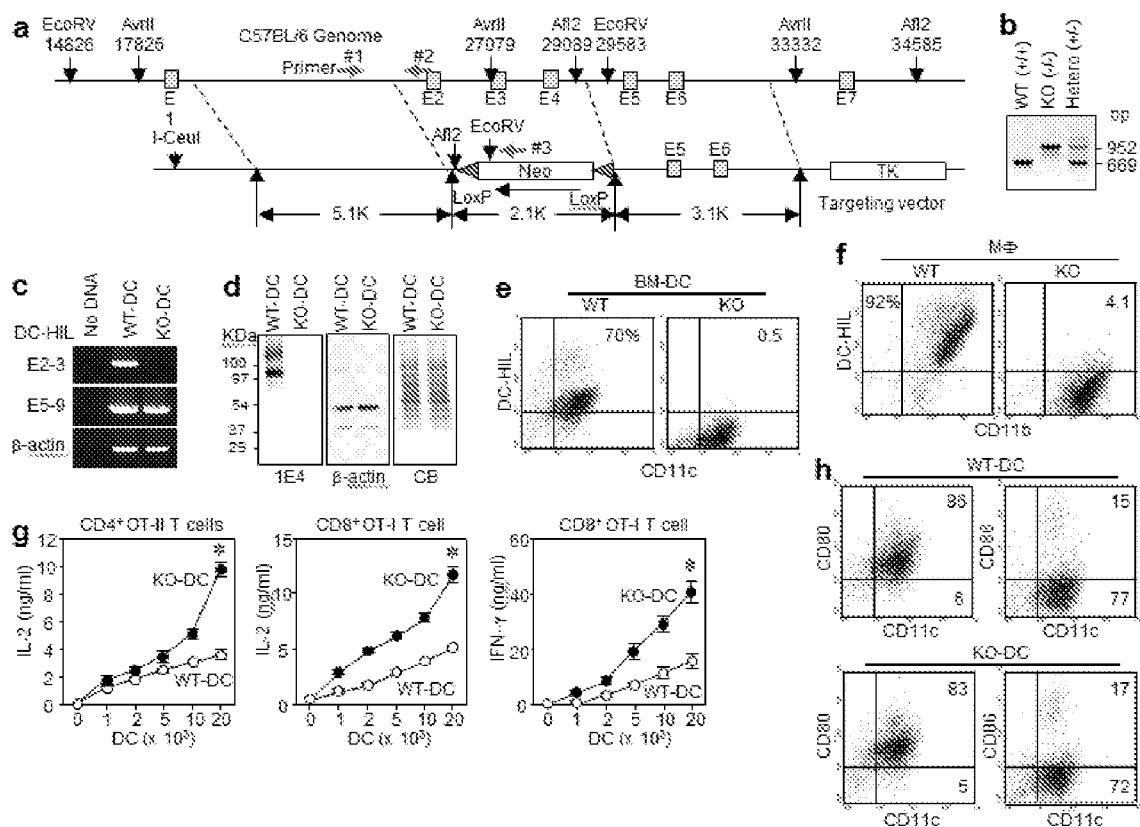
FIGS. 1A-H. Characterization of DC-HIL-deficient APC.

DC-HIL mRNA expression in KO mice was examined by RT-PCR analysis of total RNA isolated from BM-derived DC (BM-DC) using 2 primer sets: the first to amplify exons 2-3 (within targeted region), and the second for exons 5-9 (downstream) (FIG. 1C). The first primer amplified RNA from DC of WT mice, but not of KO mice; and the second primer produced PCR product from both RNA samples, indicating that KO mRNA lacked targeted exons but bore the remaining downstream 5-9 exons. The inventors then probed for DC-HIL protein using 2 mAb (FIG. 1C), UTX103 rabbit anti-DC-HIL and 1E4 rat anti-DC-HIL mAb, whose epitopes are encoded by exons 2 and 8, respectively. Both mAb stained 2 bands (95 and 120 KDa) from extracts of DC from WT mice (but not from KO mice) (FIG. 1D). Control β-actin expression was similar for both. Moreover, UTX103 mAb failed to show surface expression of DC-HIL on KO-DC (FIG. 1E). There was no significant difference in the frequency of CD11c+ cells among GM-CSF-cultured BM cells (91% for WT vs. 88% for KO). Similar results were shown for macrophages (FIG. 1F).

The inventors did not observe any gross abnormality or developmental defect in lymphoid organs of KO mice, and there was no significant difference in the proportions of leukocyte subpopulations compared to WT (data not shown). The inventors then evaluated the capacity of DC-HIL$^{-/-}$ DC to activate syngeneic OVA-specific T cells (FIG. 1G). Increasing numbers of DC from WT or KO mice were cocultured with CD4+ or CD8+ T cells in the presence of OVA peptides. DC-HIL$^{-/-}$ DC stimulated naive CD4+ and CD8+ T cells to produce IL-2 and IFN-γ at 2-fold greater levels than DC-HIL$^{+/+}$ DC. Since lack of DC-HIL had no impact on constitutive expression of costimulatory receptors (CD80 and CD86, FIG. 1H), these results confirm DC-HIL receptor to be a negative regulator on APC.

Figure 2:
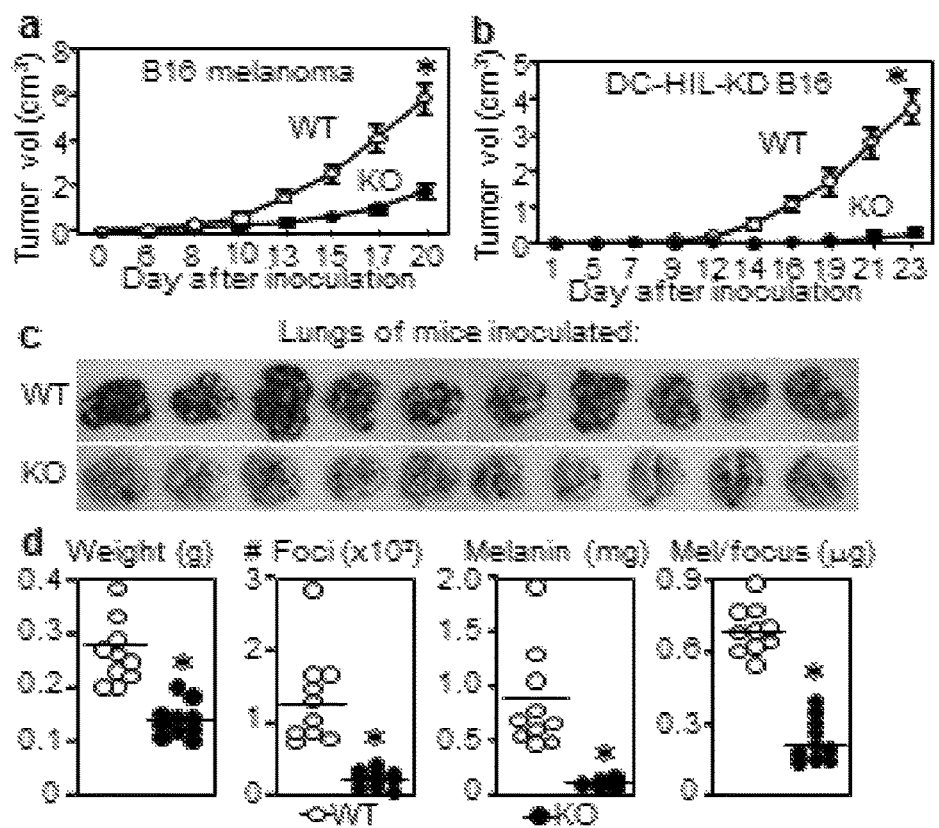
FIGS. 2A-D. Growth and metastasis of B16 melanoma are suppressed in $DC-HIL^{-/-}$ mice.

Deletion of DC-HIL Gene in Mice Inhibits Growth of Subcutaneous and Metastatic Melanoma The inventors next employed DC-HIL$^{-/-}$ mice to assess influence of DC-HIL on melanoma growth. DC-HIL-KO or WT mice were inoculated s.c. with B16 melanoma cells (FIG. 2A). Growth of subcutaneous melanoma was aggressive in WT mice, but markedly inhibited in KO mice (2.5±0.3 vs. 0.6±0.1 cm3 on day 15). They then examined impact of DC-HIL deletion on lung metastasis (or spreading to lung) (FIGS. 2C-D). WT or KO mice were infused with B16 cells via the tail vein, and their lungs examined after 19 days: Compared to WT mice, KO mice had markedly lighter lungs (0.28±0.06 g for WT vs. 0.15±0.02 g for KO), less metastatic foci (1,280±636 vs. 194±105), less melanin content per lung (0.89±0.44 vs. 0.045±0.021 mg), and less melanin per metastatic focus (0.7±0.1 vs. 0.2±0.08 µg).

The inventors' previous finding that DC-HIL on B16 melanoma cells promotes melanoma growth by suppressing T cell activation prompted examination of the influence of melanoma-expressed DC-HIL on the tumor growth inhibition in DC-HIL KO mice. DC-HIL-knocked down B16 (KD-B16) cells were subcutaneously implanted into WT or KO mice, and tumor growth measured (FIG. 2B). KD-B16 cells grew in WT mice more slowly than parental B16 cells (Tomihari et al., 2010), and this slow growth was also markedly inhibited in KO mice. These results indicate that host-associated DC-HIL fuels aggressive tumor growth, independent of melanoma-associated DC-HIL.

Among DC-HIL+ Myeloid Cells in Mice Bearing Melanoma, CD11b+Gr-1+ Cells are the Major Population Responsible for the Most Potent T Cell-Suppressive Activity.

Because DC-HIL is expressed by APC or myeloid cells (but not by lymphocytes) in spleen of naive or immunized mice (Chung et al., 2009), the inventors wanted to know which DC-HIL+ myeloid cells exerted the most influence on melanoma growth. The inventors analyzed the phenotype of spleen cells expressing DC-HIL in mice bearing B16 melanoma (FIGS. 2A-B). Proportions of CD11c+ DC or F4/80+ macrophages were mildly increased (6-7%) compared with tumor-free mice (3-5%). After implantation of B16 melanoma, the most dramatically expanded myeloid population was CD11b+Gr-1+ cells (10-fold increase of 2% to 20%). Moreover, % of DC-HIL+ cells was markedly increased in all 3 populations (50-80%), but the CD11b+Gr-1+ phenotype was the major DC-HIL+ myeloid population in spleen (~10%). The inventors refer to this phenotype as myeloid-derived suppressor cells (MDSC).

Figure 3:
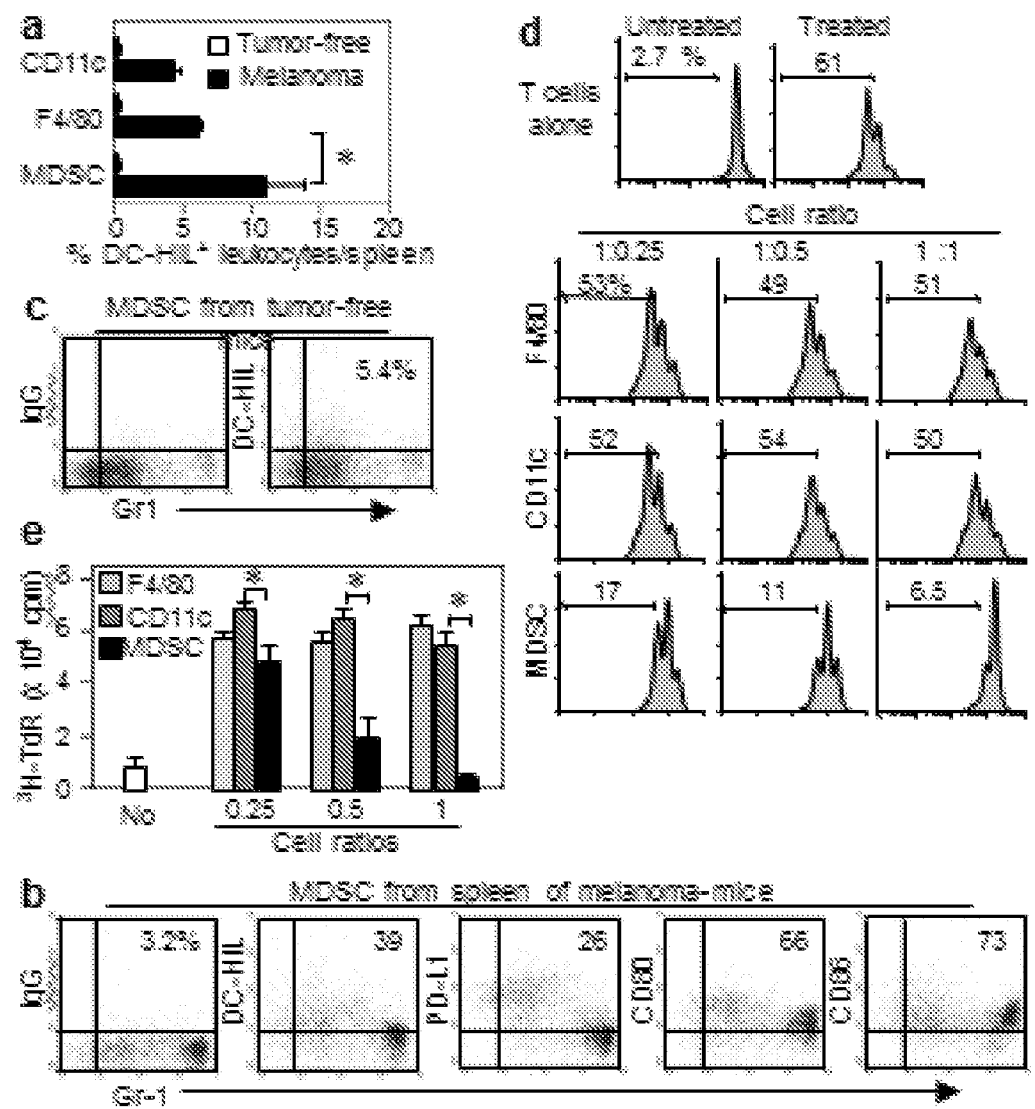
FIGS. 3A-E. Melanoma induces DC-HIL expression by most potent MDSC suppressors.

Since DC-HIL is a negative regulator of T cell activation, the inventors examined which DC-HIL+ myeloid subset is the most potent suppressor in mice bearing melanoma (FIG. 3D). Each myeloid population was purified from melanoma-bearing mice and cocultured with naive T cells activated by anti-CD3/CD28 Ab, and T cell activation measured by CFSE proliferation assay. In the absence of myeloid cells, the costimulation caused 61% of T cells to proliferate in 2 days. F4/80+ macrophages and CD11c+ DC were unable to inhibit such T cell activation even at a high cell rat(1:1), whereas MDSC inhibited it in a dose-dependent manner and with almost complete suppression at the highest ratio. Because DC and macrophages are considered APC, the inventors assayed their T cell-stimulatory capacity in comparison to MDSC (FIG. 3D). Naive CD8+ T cells from pmel-1 TCR transgenic mice (in which all CD8+ T cells express the same TCR specific to gp100 peptide (Overwijk et al. 2003)) were mixed with different myeloid cells pulsed with gp100 peptide. At a cell ratio of 1:0.5, CD11c+ DC or F4/80+ macrophages induced strong T cell proliferation. Increasing the dose (1:0.5 and 1:1) did not further augment T cell activation, indicating 1:0.25 as the peak dose. At the same dose, MDSC also exhibited similar T cell-stimulatory capacity, but increasing doses led to less proliferation to almost complete suppression. Thus, MDSC are the most potent suppressors among DC-HIL+ myeloid cells induced by melanoma.

DC-HIL is Expressed by MDSC in Melanoma-Bearing Mice.

Figure 4:
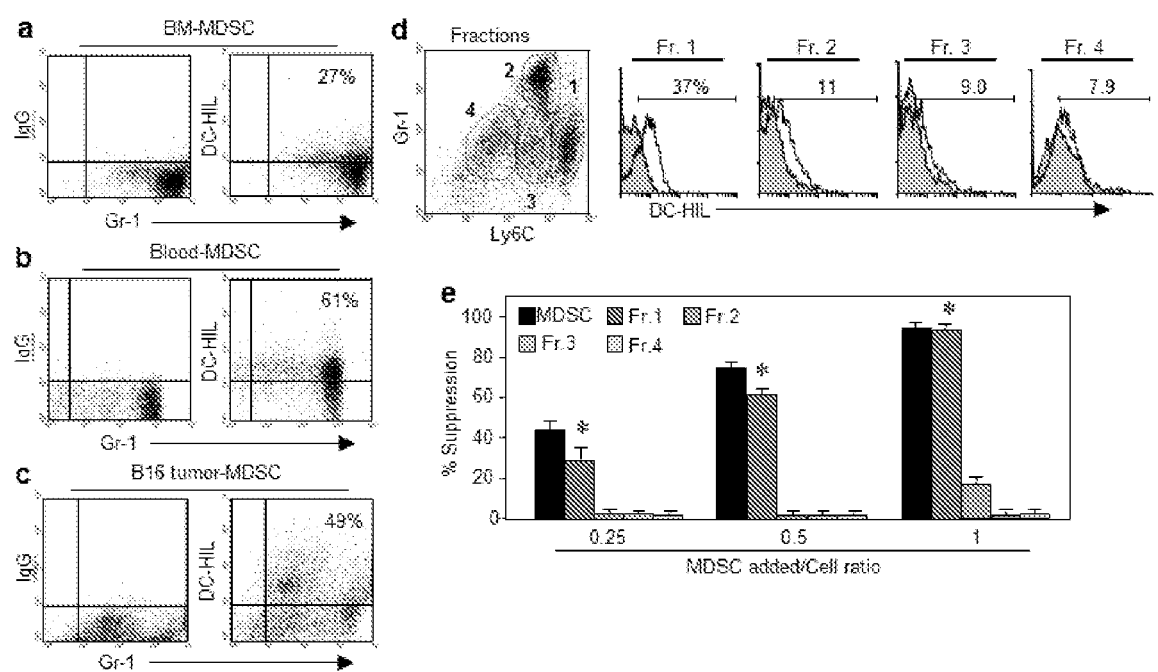
FIGS. 4A-E. DC-HIL is expressed by some MDSC from several tissues. Three weeks after implanting B16 melanoma cells in mice, $CD11b^+Gr1^+$ MDSC were purified from different tissues and examined for DC-HIL expression by FACS.

The inventors then examined expression of DC-HIL on MDSC purified from mice with melanoma (FIG. 3B). Purified MDSC were fractionated into the Gr-1low monocytic (21%) and the Gr-1hgh granulocytic subsets (75%) (Movahedi et al., 2008 and Peranzoni et al., 2010). They compared expression of DC-HIL with other coinhibitory ligands expressed by MDSC (FIG. 3B). DC-HIL was expressed by 40% of MDSC (40-60% of either subset), PD-L1 by 26% (all of which were Gr-1low cells; rarely Gr-1high cells), and CD80 and CD86 by 66-73% regardless of subset. Importantly, MDSC isolated from tumor-free mice did not express DC-HIL at all (FIG. 3B). More rigorously, they examined DC-HIL expression by MDSC subsets (FIG. 4C). CD11b+ Gr-1+ MDSC sorted into 4 subsets based on differential expression of Ly6C vs. Gr-1 (Elkabets et al., 2010). The fraction distinguished by Ly6ChighGr-1low phenotype (designated Fr. 1) expressed highest levels of DC-HIL (37%); Ly6CmedGr-1high (Fr. 2) contained 11% DC-HIL+ cells; and the other 2 fractions (Ly6CmedGr-1low and Ly6ClowGr-1low) expressed minimal DC-HIL just above background level. The inventors also determined the macrophage component of each fraction (FIG. 4E). Frs. 1 and 4 expressed low levels of F4/80 (14 and 18%, respectively); Fr. 2 was mixed with a small but distinct population of macrophages (23%); and Fr. 3 contained 45% macrophages.

Since MDSC phenotype within tissues may be heterogenous (Gabrilovich and Nagaraj, 2009), the inventors examined whether DC-HIL is expressed by these cells in tissues other than spleen. MDSCs isolated from BM, peripheral blood, and from the tumor site of melanoma-bearing mice, were assayed for DC-HIL expression. DC-HIL was expressed by 30% of MDSC from BM (FIG. 4A), 61% from blood (FIG. 4B), and 60% from the B16 tumor site (FIG. 4C). These results indicate that melanoma induces DC-HIL expression on MDSC in many organs, particularly of the Ly6ChighGr-1low subset.

DC-HIL Mediates the T Cell-Suppressive Function of MDSC.

Figure 5:
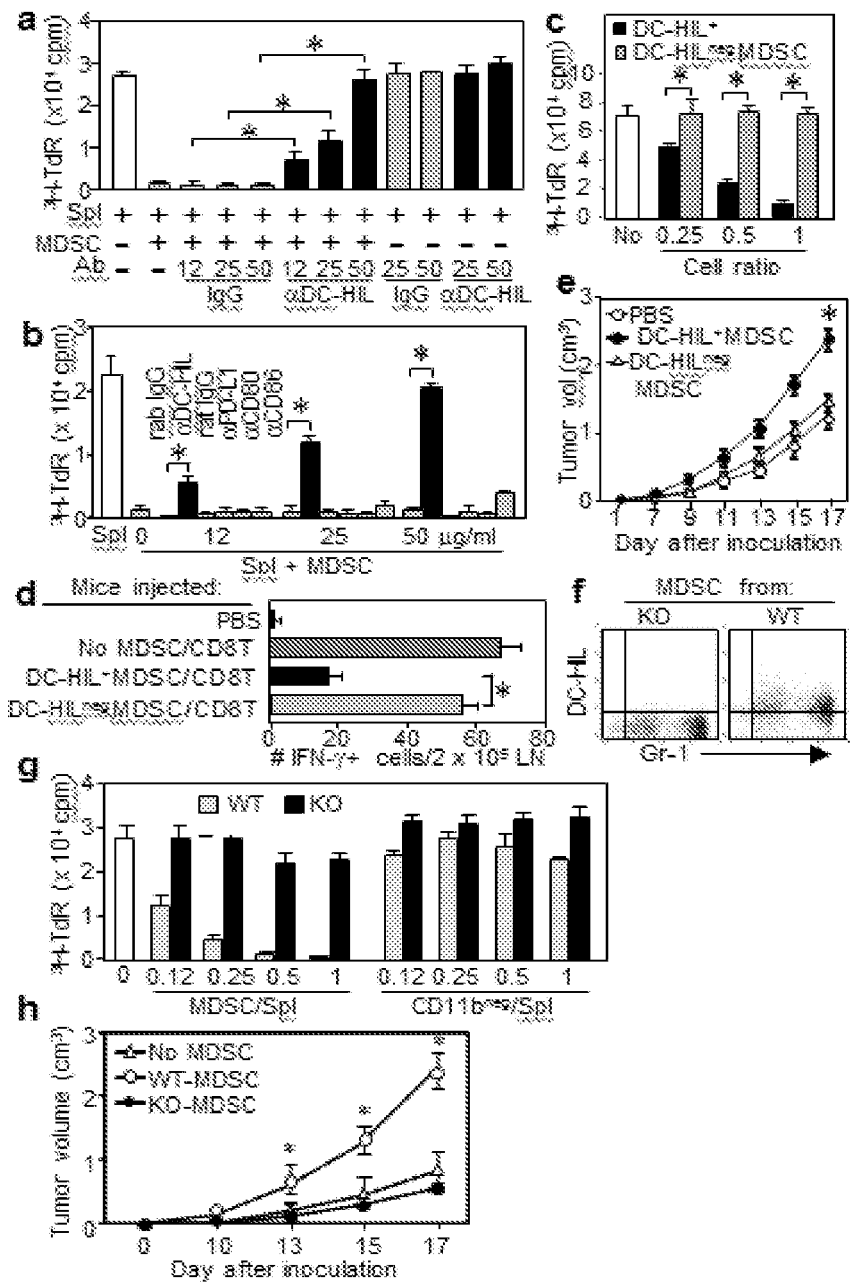
FIGS. 5A-H. DC-HIL mediates T cell-suppressor activity of MDSC.

The inventors then addressed whether MDSCs require DC-HIL expression to suppress T cell activation. CD11b+ Gr-1+ MDSC from melanoma-bearing mice (melanoma-MDSC) were incubated with pmel-1 spleen cells in the presence of gp100 peptide at a 1:1 cell ratio. The inventors added UTX103 anti-DC-HIL mAb (or control IgG) to block the function of DC-HIL expressed by MDSC (FIG. 5A). UTX103 mAb (but not control IgG) restored pmel-1 T cell activation dose-dependently, with complete restoration at the highest dose. Because APC in pmel-1 splenocytes express DC-HIL albeit at a lower level, they probed its influence by adding anti-DC-HIL mAb to spleen cells with Ag but without MDSC. Neither UTX103 mAb nor control IgG affected T cell activation, indicating DC-HIL on spleen APC had no influence. The inventors also probed a role for other coinhibitory ligands (FIG. 5B). Reproducibly, UTX103 mAb blocked suppression completely, whereas anti-CD80 or anti-PD-L1 Ab did not; highest concentration of anti-CD86 Ab increased proliferation just 17%. Among coinhibitory ligands examined, DC-HIL was the only receptor capable of mediating the suppressor activity of MDSC.

DC-HIL+ MDSC Subset is the Most Potent Suppressor Among the Total MDSC Induced by Melanoma Because only some (not all) MDSC induced by melanoma express DC-HIL (FIG. 3B) and because MDSC requires DC-HIL expression for their function (FIG. 5A), the inventors posited that DC-HIL+ MDSC are responsible for suppressor activity. Because DC-HIL expression was confined to the Fr. 1 subset, the inventors determined whether DC-HIL+ MDSC are more potent suppressors than other subsets (Frs. 2-4). Unfractionated as well as the 4 FACS-sorted fractions were added separately to culture of pmel-1 spleen cells with gp100 peptide, and suppressive ability assayed (FIG. 4E). Unfractionated MDSC inhibited T cell activation almost completely (100% suppression); Fr 1 (with highest DC-HIL expression level) also exhibited similarly strong activity; Fr. 2 exhibited weak activity even at highest dose; and Frs 3 and 4 had no effect on T cells.

Because Fr. 1 was contaminated with DC-HIL$^{neg}$ cells, the inventors employed a depletion strategy to examine whether DC-HIL+ MDSC are the potent suppressors. DC-HIL+ cells were depleted from total CD11b+Gr-1+ melanoma-MDSC and assayed for ability to suppress Ag-specific and nonspecific T cell activation. Reproducibly, untreated MDSC inhibited gp100-triggered T cell activation almost completely, whereas depletion of DC-HIL+ cells abrogated the ability at every dose examined (FIG. 5C).

The inventors also questioned whether DC-HIL+ MDSC can induce CD8+ T cell suppression in mice. On day 0, mice were injected with naive pmel-1 CD8+ T cells, and on day 3 were given untreated or DC-HIL-depleted MDSC and vaccinated with gp100 peptide. Ten days later, draining LN cells were prepared and IFN-γ-secreting cells counted (FIG. 5D). Mice infused with CD8+ T cells but without MDSC produced very high numbers of IFN-γ-T cells (61.6±7.0 cells/2×10$^5$ LN cells). This number was markedly decreased by co-infusion of untreated MDSC (containing DC-HIL+ cells) (down to 13±2 cells), whereas suppression was abrogated by depletion of DC-HIL+ cells from the MDSC preparation (60±5 cells). Altogether, these results indicate that the DC-HIL+ subset is responsible for suppressor activity and for immunosuppression by CD11b+Gr-1+ MDSC in melanoma-bearing mice.

Deletion of DC-HIL Abrogates MDSCs Ability to Suppress T Cell Activation and to Promote Melanoma Progression.

The inventors next studied the impact of DC-HIL gene deletion on MDSC function. MDSC isolated from DC-HIL KO or WT mice bearing melanoma were assessed for their capacity to suppress activation of pmel-1 T cells. MDSC-depleted fraction (CD11b$^{neg}$) was also isolated from the same mice (control). Varying numbers of MDSC or CD11b$^{neg}$ cells were cocultured with pmel-1 spleen cells plus Ag, and their proliferation measured (FIG. 5G). DC-HIL$^{+/+}$ MDSC inhibited proliferation dose-dependently, with complete inhibition at 1:1 cell ratio. By contrast, DC-HIL$^{-/-}$ MDSC failed to inhibit T cell activation, except for minuscule effect at the highest ratio. CD11b$^{neg}$ cells from WT or KO mice showed no inhibition. DC-HIL$^{-/-}$ MDSC were confirmed to not express DC-HIL (FIG. 5G).

To assess the ability of MDSCs to promote melanoma growth, the inventors purified melanoma-MDSC and co-injected them with B16 cells s.c. into naive WT mice. A week later, melanoma-MDSC alone were infused i.v. into corresponding mice (FIG. 5H). Melanoma in mice co-injected with DC-HIL$^{+/+}$ MDSCs grew significantly larger than in mice injected with B16 cells alone (0.9±0.2 vs. 2.6±0.3 cm$^3$ by day 17). By contrast, melanoma in mice co-injected with DC-HIL$^{-/-}$ MDSCs grew similarly as control (without MDSC). Loss of DC-HIL expression most likely led to reduced ability to suppress T cell activation and promote melanoma growth.

Figure 6:
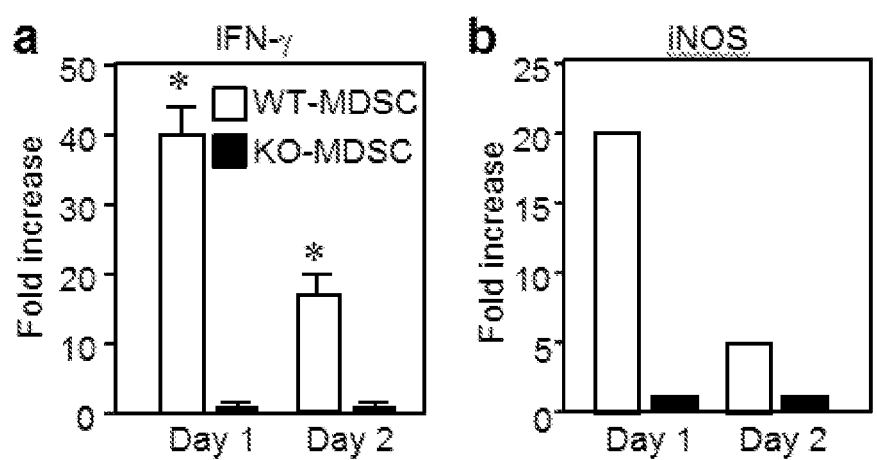
FIGS. 6A-B. MDSC are unable to induce expression of IFN-γ and iNOS following DC-HIL-crosslinking. MDSC isolated from WT or DC-HIL KO mice (n=3) bearing melanoma were DC-HIL-crosslinked and assayed (FIG. 6A) for IFN-γ production (by ELISA) and (FIG. 6B) for iNOS mRNA expression (by real time PCR): the former was measured individually by MDSC (mean±sd, n=3); and the latter by pooled MDSC. Data are shown as fold increase (anti-DC-HIL-treated culture vs. control IgG). Data are representative of 2 experiments. *p<0.001 between WT and KO.

To examine the possibility that deficient function of DC-HIL$^{-/-}$ MDSCs resulted from reduced expression of soluble inhibitory mediators, melanoma-MDSC from WT or KO mice were compared for NO production, arginase activity, and ROS (FIGS. 6A-B). DC-HIL$^{-/-}$ MDSCs expressed 30% lower NO (13.3±1.6 vs. 19.1±2.3 µM) and 40% lower arginase activity (0.9±0.2 vs. 1.5±0.2 U/L) than WT control, whereas ROS was similar for both. Thus, DC-HIL deficiency led to 30-40% reduction in constitutive expression of NO and arginase I. Because such impact is not sufficient to account for the much greater loss of suppressor activity by DC-HIL$^{-/-}$ MDSC, the inventors do not think that constitutively low levels of soluble mediators accounted for loss of suppressor activity by DC-HIL−/− MDSC.

IFN-γ and NO Also Mediate the T Cell-Suppressive Activity of MDSCs.

Figure 7:
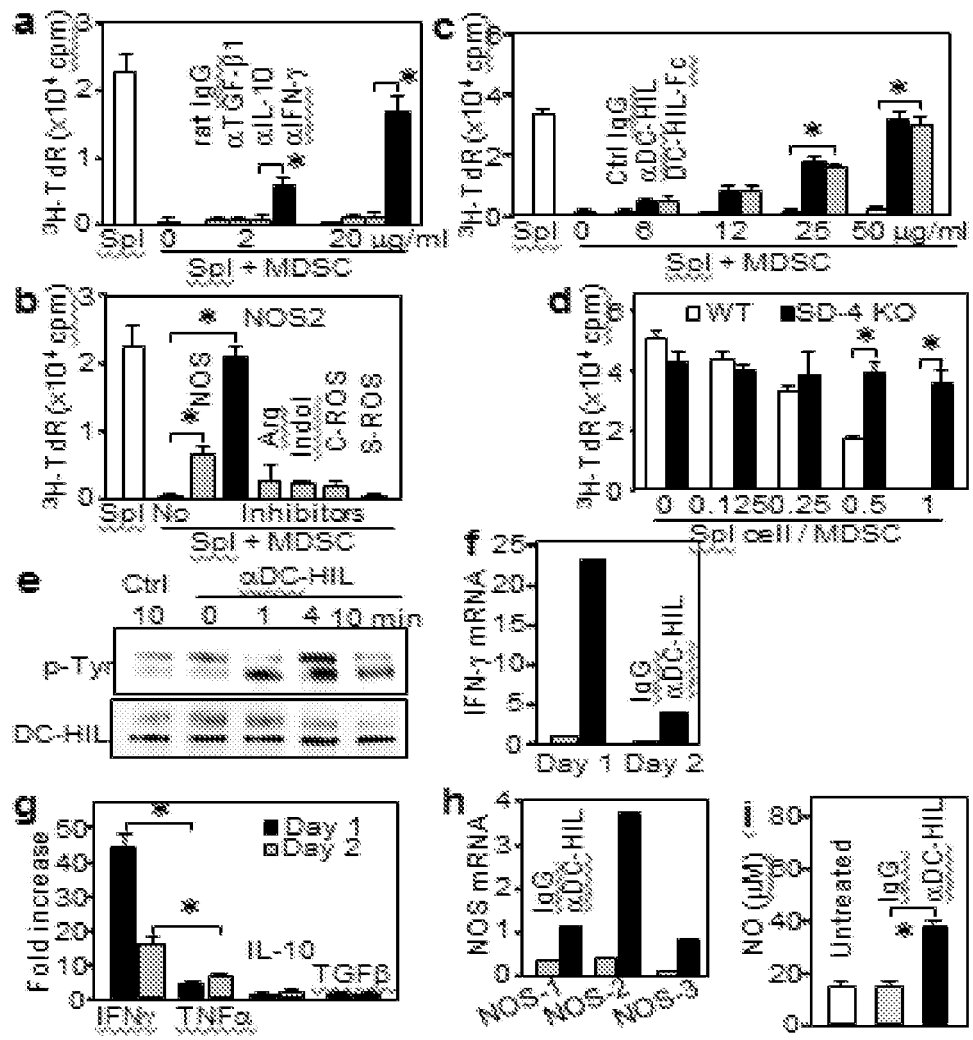
FIGS. 7A-I. Crosslinked DC-HIL on MDSC induces tyrosine phosphorylation and IFN-γ/iNOS expression.

Various soluble inhibitory mediators and cytokines were shown to mediate suppression by MDSCs, but with no consistency among tumor models (Gabrilovich and Nagaraj, 2009). The inventors thus wanted to identify soluble factors responsible for MDSC activity, independent of DC-HIL, by adding specific inhibitors to cocultures of pmel-1 spleen cells and melanoma-MDSC. Neutralizing Ab to TGF-β (Filipazzi et al., 2007) or IL-10 (Wang et al., 2010) had no effect, whereas anti-IFN-γ Ab blocked suppression completely (FIG. 7A). N-hydroxyl-nor-arginine (inhibitor of arginase activity) or 1-methyl-tryptophan (indoleamine inhibitor) restored T cell activation marginally (FIG. 7B). Catalase and superoxide dismutase (ROS inhibitors) had little-to-no effect. By contrast, L-NG-monomethyl-arginine citrate (NOS inhibitor) or N6-(1-iminoethyl)-L-lysine (NOS-2 inhibitor) blocked MDSC function. Thus, IFN-γ and NOS-2 independently support the suppressor activity of MDSC induced by B16 melanoma.

T Cell Expression of SD-4 is Required for MDSC Suppressor Activity.

Since ligation of SD-4 on activated T cells is required for DC-HIL on APC to mediate inhibition (Chung et al., 2007), the inventors posited a similar mechanism for MDSC. They tested the ability of melanoma-MDSC to inhibit activation of pmel-1 spleen cells in the presence of DC-HIL-Fc, which interferes with DC-HIL/SD-4 binding (Chung et al., 2007). Like UTX103 mAb, DC-HIL-Fc restored T cell activation dose-dependently (up to 90%), whereas control Ig did not (FIG. 7C). For SD-4 specificity, the inventors compared MDSCs ability to suppress activation of SD-4$^{+/+}$ vs. SD-4$^{-/-}$ pmel-1 spleen cells triggered by gp100 Ag (FIG. 7D). Without MDSC, spleen cells from both mice exhibited similar capacity to induce T cell proliferation; whereas addition of MDSC to spleen cells inhibited SD-4+/+ T cell activation dose-dependently (completely at 1:1 cell ratio), while only 15% inhibition was achieved for SD-4$^{-/-}$ T cells at highest ratio. Thus, melanoma-MDSC are likely to inhibit T cell activation via SD-4.

Crosslinking of DC-HIL Induces Tyrosine Phosphorylation Leading to Expression of IFN-γ and NOS-2 (iNOS) in MDSCs.

Since DC-HIL has an immunoreceptor tyrosine-based activation motif (ITAM) in its intracellular domain (Shikano et al., 2001), the inventors posited that binding of DC-HIL to SD-4 not only inhibits T cell activation via SD-4 signals but also activates MDSC function via ITAM-induced signals. They determined whether ligation of DC-HIL triggers tyrosine phosphorylation of the ITAM in MDSCs. DC-HIL on melanoma-MDSC was cross-linked with UTX103 mAb, and expression of tyrosine-phosphorylation on DC-HIL examined (FIG. 7E). Tyrosine phosphorylation on DC-HIL was induced in MDSCs as early as 1 min following cross-linking of the receptor, whereas control IgG induced only basal level. Amounts of DC-HIL protein were similar among immunoprecipitate samples. The tyrosine phosphorylation is likely to occur on the ITAM, as shown previously using transfection experiments (Chung et al., 2009).

Having shown that DC-HIL, IFN-γ and NOS-2 are independent mediators for the suppressor activity of MDSC, the inventors posited that all 3 components participate in a cascade initiated by DC-HIL-linked tyrosine phosphorylation. The inventors thus examined expression of IFN-γ mRNA in MDSC after cross-linking DC-HIL receptor (FIG. 7F). IFN-γ mRNA was markedly increased (20-fold greater than control) one day after cross-linking of DC-HIL, and quickly decreased (but still 4-fold greater) next day. To address specificity of cross-linking to IFN-γ, the inventors measured cytokine secretion by MDSC treated with to UTX103 mAb (FIG. 7G). Among cytokines examined, IFN-γ was the most responsive cytokine, increasing 45-fold compared to control treatment on day 1 after cross-linking.

TNF-α secretion also increased, but only 4-5-fold higher than control. Expression of IL-10 and TGF-β, which were not involved in suppressor activity (FIG. 7A), were unchanged. The inventors then examined expression of NOS-1, NOS-2, and NOS-3 mRNA (FIG. 7H). Cross-linking DC-HIL on MDSC induced NOS-2 expression 4-fold greater than control; it was the most abundantly expressed among the 3 types of NOS, consistent with known NOS-2 inducibility by IFN-γ (Kamijo et al., 1994). Such high expression was supported by increased level of NO after cross-linking DC-HIL on MDSCs (FIG. 7I).

Anti-DC-HIL Treatment of Melanoma-Bearing Mice Suppresses Tumor Growth and Reduces Circulating MDSC.

Figure 8:
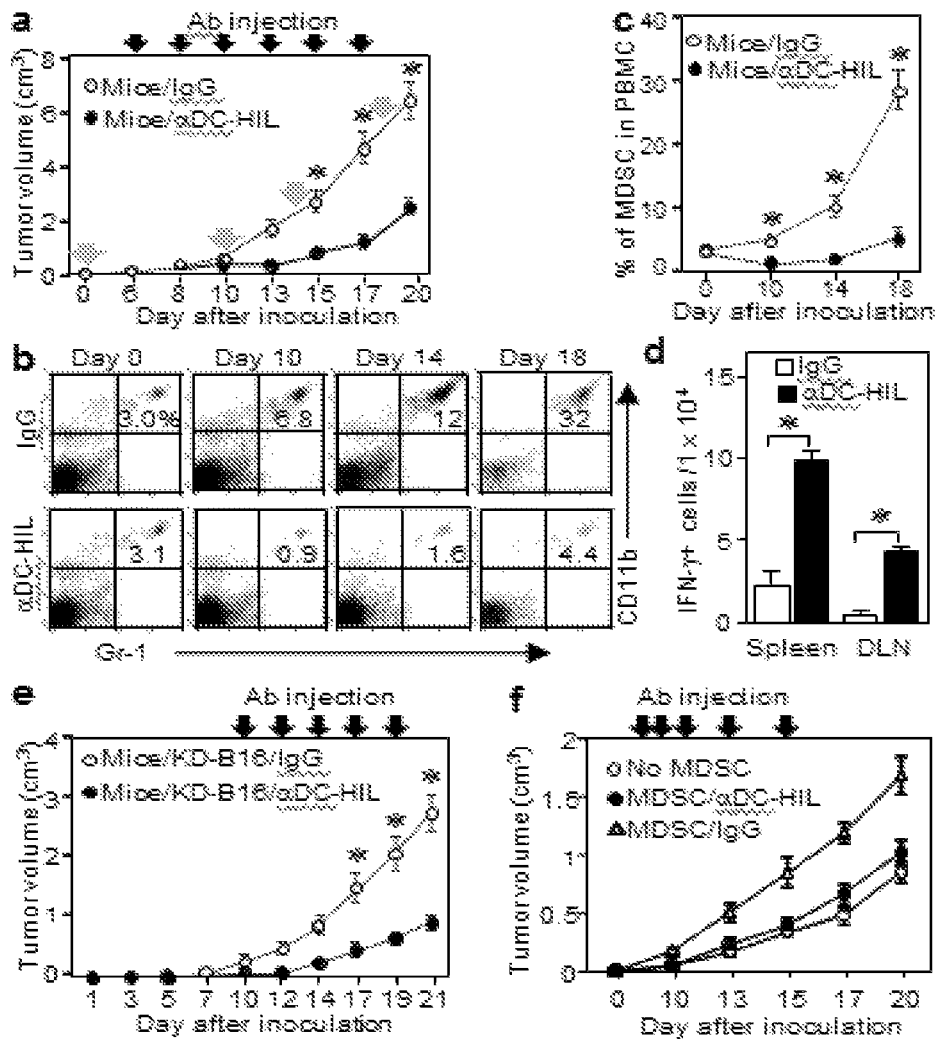
FIGS. 8A-F. Infusion of anti-DC-HIL mAb suppresses melanoma growth and expansion of MDSC.
Figure 9:
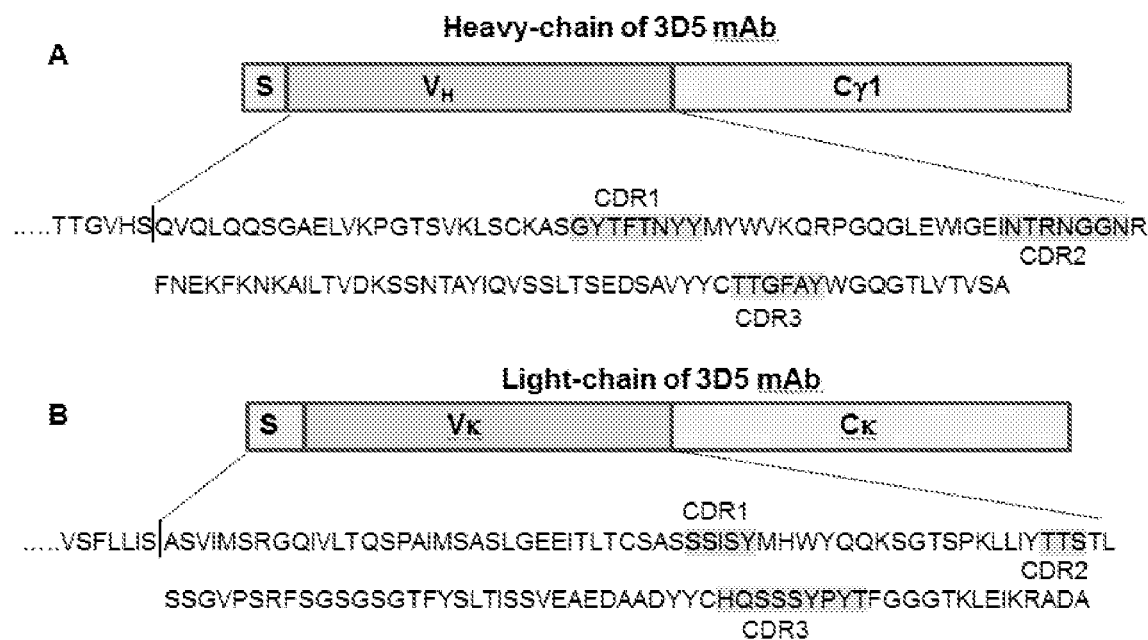
FIGS. 9A-B. Amino acid sequences of 3D5 mouse anti-human DC-HIL mAb. Total RNA isolated from 3D5-producing B cells is reverse-transcribed to cDNAs and PCR-amplified with primers: (1) for V$_H$ region, 5'-RCTACAGGTGTCCACTCC-3' (encoding the signal peptide; SEQ ID NO: 20) and 5'-TAGCCCTTGACCAG-GCATCC-3' (the C$_H$ region; SEQ ID NO: 21); and (2) for Vk region, 5'-TCAGCTTCYTGCTAATCAGTG-3' (the signal peptide; SEQ ID NO: 22) and 5'-TGGTGGGAAGATGGA-TACAG-3' (the Ck region; SEQ ID NO: 23). Resulting PCR product was ligated to pCR2.1 vector, and the insert was determined for DNA sequences, from of which amino acid sequences were deduced. CDR sequences (shown in green) in the V$_H$ (FIG. 9A) and Vk (FIG. 9B) regions were determined using IMGT programs. (A, heavy-chain=SEQ ID NO: 9; B, light-chain=SEQ ID NO: 8)

Since anti-DC-HIL mAb blocks MDSC suppressor function, the inventors assessed effects of UTX103 mAb on melanoma growth. Because MDSC started to accumulate in spleen 6 days after tumor inoculation (tumors grew to ~0.1 cm$^3$) (Cheng et al., 2008), they injected UTX103 mAb or control IgG i.p. on this date and every other day after, for 6 treatments. In mice treated with control IgG, melanoma grew aggressively after day 10, in proportion to frequency of MDSCs in blood, which increased from 3% on day 0 to 32% on day 18. Treatment with UTX103 mAb markedly suppressed subsequent growth of melanoma (FIG. 8A) and prevented MDSC from expanding in blood (FIG. 8B-C). Thus, anti-DC-HIL mAb treatment suppresses growth of established melanoma and blocks expansion of MDSCs.

Inhibited MDSC Function Accounts for the Therapeutic Effects of Anti-DC-HIL mAb on Melanoma.

Having shown melanoma to express DC-HIL with inhibition of T cell activation (Chung et al., 2007 and Tomihari et al., 2010), the inventors probed the basis for beneficial outcomes of UTX103 mAb. For DC-HIL+melanoma, they implanted WT mice with DC-HIL-knocked-down B16 cells (KD-B16) (Tomihari et al., 2010) instead of parental cells, with Ab injected starting day 11 and every other day after, for 5 treatments (FIG. 8D). In this assay, both MDSC and APC were DC-HIL+ cells. KD-B16 tumor grew to 3.0 cm$^3$ by day 21 in mice injected with control IgG, but its growth was inhibited markedly (1.0 cm$^3$) in mice treated with UTX103 mAb, negating the significant involvement of DC-HIL on melanoma to the effects of anti-DC-HIL mAb.

For DC-HIL+ APC (FIG. 8E), BM-DC were pulsed with gp100 peptide and infused into DC-HIL-/- mice bearing melanoma (~0.2 cm$^3$), that were then injected with CFSE-labeled pmel-1 T cells. On days 0 and 2, UTX103 mAb or control IgG was injected. Mice injected with unpulsed DC and pmel-1 T cells served as control. On day 3, spleen or LN cells were harvested and examined for CFSE fluorescence intensity of infused Thy1.1+ T cells. In this assay, both B16 cells and adoptively transferred DC were DC-HIL+ cells. Proliferating pmel-1 T cells in spleen and LN of mice injected with Ag-pulsed DC/control IgG were significantly higher than in mice injected with unpulsed DC. However, the proportion of proliferating T cells was not significantly augmented by UTX103 mAb, indicating that infused anti-DC-HIL mAb had little-to-no effect on APC function of DC.

DC-HIL+ MDSC are Expanded in Blood of Melanoma Patients.

Figure 12:
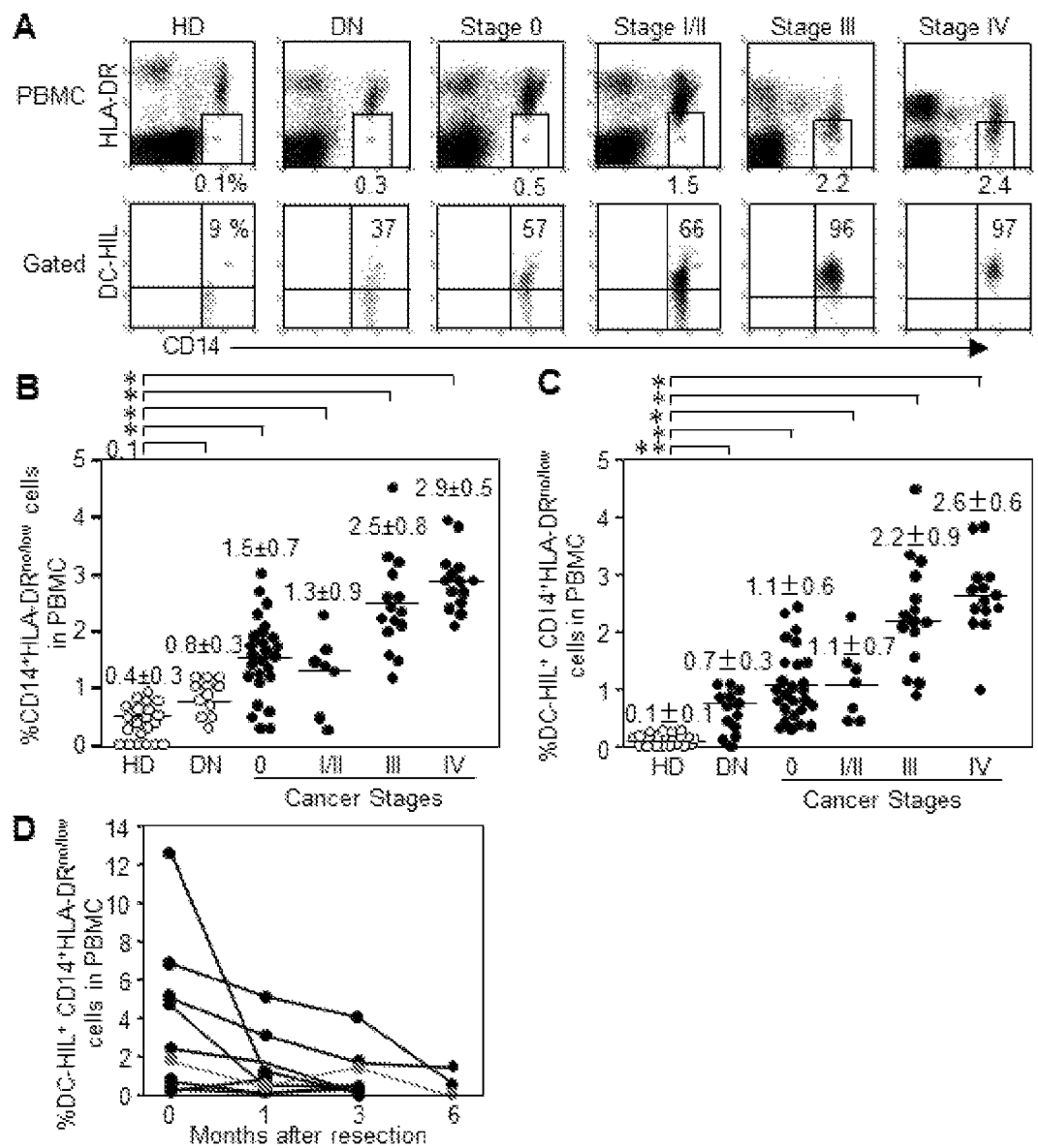
FIGS. 12A-D. Positive correlation between blood DC-HIL⁺CD14⁺HLA-DR$^{no/low}$ myeloid-derived suppressor cells (MDSCs) and melanoma stage. Peripheral blood mononuclear cells (PBMCs) from melanoma patients (stages 0-IV, referred to FIG. 5) or dysplastic nevus (DN), and from healthy donors (HD) were analyzed for CD14 vs. HLA-DR expression, in which CD14$^{30}$HLA-DR$^{no/low}$ MDSCs are indicated (%). These cells were FACS-gated and examined for expression of DC-HIL vs. CD14. Data shown are representative of each group (FIG. 12A). % CD14⁺HLA-DR$^{no/low}$ MDSCs (FIG. 12B) or % DC-HIL⁺MDSCs/PBMC (FIG. 12C) in each cohort is summarized (mean %±sd). Statistical significance for each stage was calculated by comparison with HD.

Since CD14$^+$HLA-DR$^{no/low}$ MDSC are the human equivalent of mouse CD11b$^+$Gr-1$^+$ MDSC (Filipazzi et al., 2007), we posited that blood CD14$^+$HLA-DR$^{no/low}$ cells in melanoma patients express DC-HIL and that such expression makes them immunosuppressive. Thus we examined blood frequencies of CD14$^+$HLA-DR$^{no/low}$ cells and their DC-HIL expression, in cases of: melanoma with varying clinical stages (0-IV) (n=62), dysplastic nevi (in which melanocytes are abnormal but not malignant (n=12)), and healthy donors (n=21) (FIG. 12A, FIG. 13). Compared to healthy donors, all cases of melanoma exhibited elevated blood CD14$^+$HLA-DR$^{no/low}$ cells (FIG. 12B), consistent with a prior report (Filipazzi et al., 2007). Whereas blood CD14$^+$HLA-DR$^{no/low}$ cells in healthy donors had little-to-no expression of DC-HIL (0.1±0.1% DC-HIL$^+$ cells among PBMCs), all cases of metastatic melanoma (stages III/IV) displayed high-level DC-HIL expression on these cells (2.9±0.9% and 2.6±0.6%, respectively; t test p=0.001 vs. healthy donors) (FIG. 12C). Intermediate levels of DC-HIL expression were seen in blood CD14$^+$HLA-DR$^{no/low}$ cells of melanoma confined to skin (stages 0/I-II). Dysplastic nevi showed lower expression than skin-restricted melanoma, but higher than for healthy donors (p=0.01). Thus blood levels of DC-HIL$^+$CD14$^+$HLA-DR$^{no/low}$ cells correlated with cancer progression, particularly in advanced stages. Other MDSC subsets (CD14$^+$IL-4Rα$^+$, CD14$^{neg}$CD11b$^+$CD15$^+$, and CD14$^{neg}$IL-4Rα$^+$CD15$^+$) also expressed DC-HIL at a range of 30-75% (FIG. 16).

To determine whether melanoma was the cause of the elevated blood levels, we followed a new cohort of 9 patients with stage 0 melanoma and assayed for % DC-HIL$^+$ CD14$^+$HLA-DR$^{no/low}$ MDSC in their PBMCs (FIG. 12D), at 0, 1, 3, and 6 months after excision of the melanoma. At the time of resection (0 month), all subjects except one (subject M83) exhibited higher levels than healthy controls (0.3 to 12.8%) (FIG. 14). Across the 3-month follow-up, these elevated levels declined significantly in 8 patients (Wald test, p=0.045) to an average of 0.4%, close to that of 6 normal controls (FIG. 15). Interestingly, in the case of one patient (M71), the % DC-HIL$^+$CD14$^+$HLA-DR$^{no/low}$ cells that declined a month post-resection climbed back to a high level at 3 months, which coincided with discovery of a new melanoma in situ (stage 0), and then fell back after resection of this second melanoma. The inventors concluded that melanoma is responsible (directly or indirectly) for acquisition of DC-HIL expression by CD14$^+$HLA-DR$^{no/low}$ cells. Because our mouse studies showed IFN-γ and IL-1β to induce DC-HIL expression by CD11b$^+$Gr1$^+$ cells, we speculate similar mechanisms for human CD14$^+$HLA-DR$^{no/low}$ cells.

DC-HIL is a Critical Mediator of the T Cell Suppressor Function of Human MDSC.

Do CD14$^+$HLA-DR$^{no/low}$ MDSC from melanoma patients suppress T-cell function and is DC-HIL responsible for that function? CD14$^+$HLA-DR$^{no/low}$ cells isolated from melanoma patients (vs. healthy donors) were cocultured with autologous T-cells activated by anti-CD2/CD3/CD28 Ab (FIG. 17A). CD14$^+$HLA-DR$^{no/low}$ cells from melanoma patients inhibited IFN-γ production by autologous T-cells dose-dependently and almost completely, whereas corresponding cells from healthy donors were weakly immunosuppressive.

Treatment with anti-DC-HIL mAb (but not control IgG) restored the T-cell IFN-γ response dose-dependently (up to 80%) (FIG. 17B, FIG. 18). Moreover, treatment of total (unfractionated) PBMCs from melanoma patients with anti-DC-HIL mAb (but not with control IgG) enhanced the IFN-γ response, and this enhancement correlated positively with melanoma staging (FIG. 17C), but negatively with IFN-γ levels from IgG-treated PBMCs (FIG. 17D).

DC-HIL$^+$ MDSC are Also Expanded in Blood of Non-Melanoma Cancer Patients.

DC-HIL expression on MDSC was also examined in blood of patients (stages III or IV) with a cancer form of cutaneous squamous cells, breast, colon, or lung (FIG. 19). DC-HIL expression is indicated as % DC-HIL$^+$ MDSC among total PBMCs. Almost all patients (n=6-10) with squamous cell carcinoma, breast, and colon cancers induced high expression of DC-HIL, compared to healthy donors. Expression was very low in lung cancers. Thus, expansion of blood DC-HIL$^+$ MDSC is not confined to melanoma.

Identification of Complementary Determining Regions (CDRs) in Mouse Anti-Human DC-HIL mAb Clones.

Figure 10:
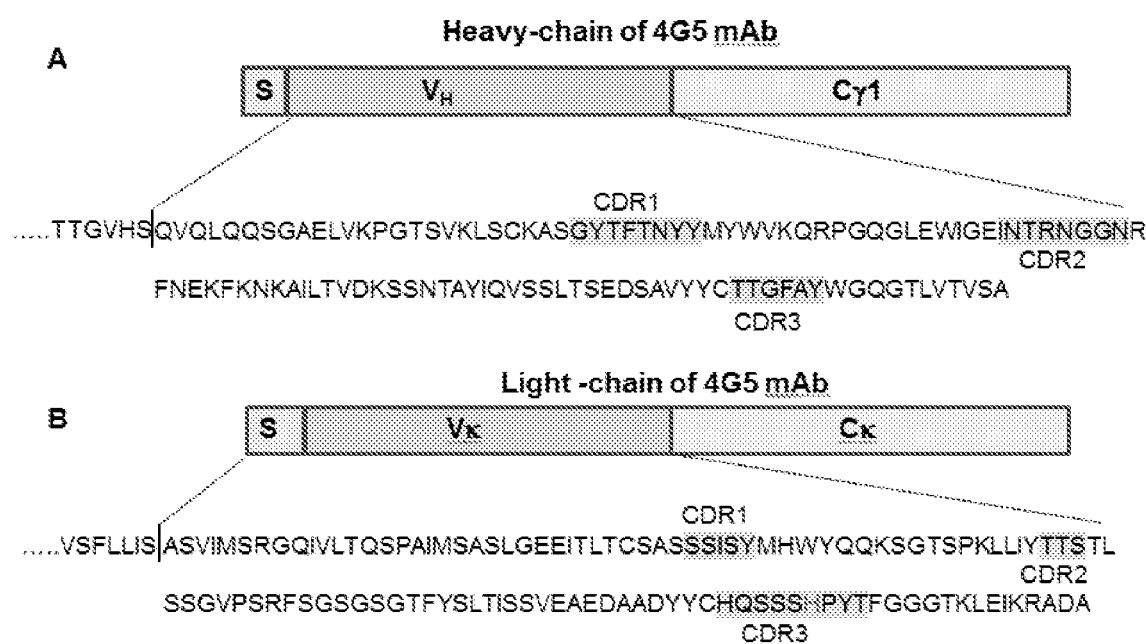
FIG. 10A-B. Amino acid sequences of 4G5 mouse anti-human DC-HIL mAb. Total RNA isolated from 4G5-producing B cells is reverse-transcribed to cDNAs and PCR-amplified with primers: (1) for V$_H$ region, 5'-RCTACAGGTGTCCACTCC-3' (encoding the signal peptide; SEQ ID NO: 20) and 5'-TAGCCCTTGACCAG-GCATCC-3' (the C$_H$ region; SEQ ID NO: 21); and (2) for Vk region, 5'-TCAGCTTCYTGCTAATCAGTG-3' (the signal peptide; SEQ ID NO: 22) and 5'-TGGTGGGAAGATGGA-TACAG-3' (the Ck region; SEQ ID NO: 23). Resulting PCR product was determined for DNA and amino acid sequences. CDR sequences in the V$_H$ (FIG. 10A) and Vk (FIG. 10B) regions are shown in green. All amino acid sequences are identical to 3D5, but with a mutation of Y→H (shown in red) in the CDR3 of the Vk region. (A, heavy-chain=SEQ ID NO: 11; B, light-chain=SEQ ID NO: 10)
Figure 11:
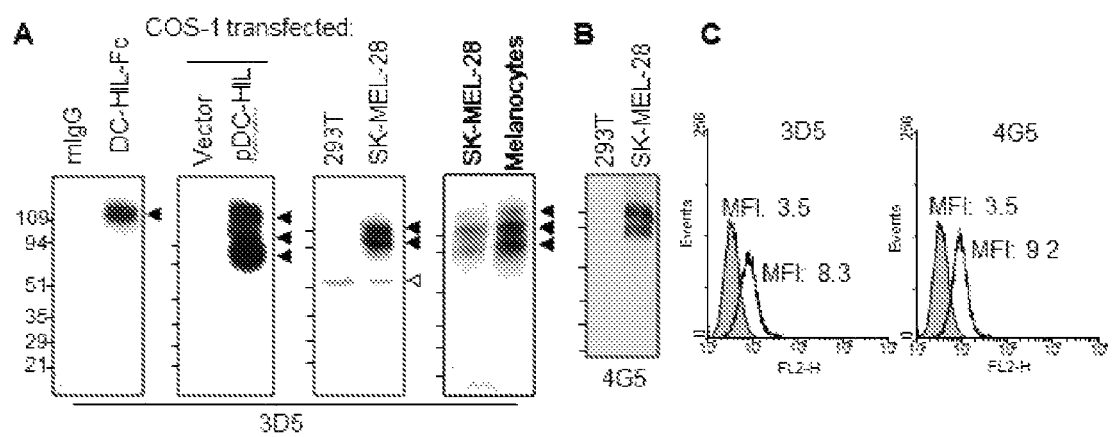
FIGS. 11A-C. Characterization of 3D5 and 4G5 mAb.

Immunization of BALB/c mice with DC-HIL-Fc recombinant protein (consisting of the extracellular domain of human DC-HIL fused to the IgG-Fc) led to the generation of 2 different mAb clones (3D5 and 4G5) with high affinity and specificity to DC-HIL protein in Western blotting and flow-cytometry (FIG. 11A-C). These clones consist of an IgG1 heavy chain and a κ light-chain. For determining DNA sequences of the mAb, total RNA isolated from the mAb clones was PCR-amplified with primers encoding for the signal peptides and for the amino acid sequences of the Cγ1 region (FIGS. 9A-B and 10A-B). The resulting PCR products were DNA-sequenced and, the amino acid sequences were deduced. Using a computer-analysis, CDRs are determined. Only one amino acid in the 3$^{rd}$ CDR of the Vκ is disparate between 3D5 (FIG. 9B) and 4G5 (FIG. 10B).

High Expression of DC-HIL on MDSC in the Blood of Patients with Cancers Other than Melanoma.

The inventors questioned whether cancers other than melanoma display high expression of DC-HIL on MDSC in the blood of patients. For this study, we recruited new cases of cancer patients with breast, colon, kidney, lung, pancreatic, and non-melanoma skin cancers (basal cell carcinoma (BCC) and cutaneous squamous cell carcinoma (SCC)). All patients were metastatic (stages III or IV) and untreated. Blood samples were taken and analyzed by flow-cytometry for frequency (%) of DC-HIL$^+$ MDSC among total peripheral blood monocytes (PBMC), using 3D5 anti-DC-HIL mAb.

The inventors' data showed that metastatic melanoma patients display 2.5% (median value) of DC-HIL$^+$ MDSC among total PBMCs, with the rage of 0.8-4.4% (FIG. 4C). Healthy controls showed 0.05%, 0.01-0.05%, n=21 (FIG. 4C). In the present studies, cancer patients who showed higher levels than melanoma are: colon cancer (median of 3.2% and the range of 0.1-27%, n=32); and kidney cancer (3.3%, 1.0-4.8%, n=5) (FIG. 25). Cancers with lower levels than melanoma but significantly higher than healthy controls are: BCC, 1.22%, 0.02-7.41%, n=29; SCC, 1.4%, 0.02-5.4%, n=25; breast cancer (1.3%, 0.5-5.5%, n=10); and pancreatic cancer (1.6%, 0.01-17%, n=10). A cancer with very low levels, but slightly higher than healthy controls, is lung cancer (0.3%, 0-5.4%, n=20). Thus, high expression of DC-HIL on MDSC in the blood is noted in patients with almost all common cancer types, except lung cancers. These results also indicate the possibility that many cancers can be targets for treatment of humanized anti-DC-HIL mAb.

Ability of 3D5 Anti-DC-HIL mAb to Neutralize the T Cell-Suppressor Function of MDSC in Varying Cancers.

Previously we showed that 3D5 anti-DC-HIL mAb treatment neutralize almost completely the T cell-suppressor function of MDSC isolated from melanoma patients, using cell culture systems. To examine whether the same mAb can similarly neutralize the function of MDSC from patients with other cancer types, MDSC and T cells were purified from the blood of the same patient and co-cultured in the presence of T cell-stimulators (magnetic beads coated with anti-CD2/CD3/CD28 Ab), with 3D5 mAb or control IgG (see the legends of FIGS. 21A-B). T cell activation was measured by IFN-γ production. Effect of 3D5 mAb was expressed as % restoration of T cell IFN-γ response that was suppressed by MDSC. The inventors performed the assays using blood samples from pancreatic cancer (n=4), colon cancer (n=6), kidney (n=2), BCC (n=2), and SCC (n=2). The effect of 3D5 mAb was variable, depending on cancer types and also on individuals. 3D5 mAb produced 80-100% restoration in all cases of pancreatic cancers (FIGS. 21A-B); 70-100% restoration for all cases of colon cancers (FIG. 22); just 25% for kidney cancers (Note: 3D5 mAb treatment increased T cell response by 20-fold greater than control IgG-treated cultures) (FIGS. 23A-B); ~20-90% for BCC; and almost no effect for SCC (FIGS. 24A-B). Note no effects of control IgG on the MDSC function. These data indicate that 3D5 anti-DC-HIL mAb can reverse the T cell-suppressor function of MDSC from not only melanoma but also from other cancers (colon, pancreatic, and kidney cancers). Thus, humanized anti-DC-HIL mAb are likely to produce beneficial outcomes in cancer patients with high expression of DC-HIL on MDSC.

Example 3—Discussion

While the important detrimental effect of an expanding population of circulating MDSC in patients with growing cancers is well established, the mechanism underlying the profound immunosuppression induced by MDSC remain unclear. Like tolerogenic APC, soluble inhibitory mediators and coinhibitory receptors were both reported to mediate MDSCs suppressor function, but no data has bridged these 2 mechanisms. The inventors now provide such linkage through the DC-HIL receptor that can trigger the IFN-γ/NOS-2 axis. Since DC-HIL expression confers the greatest suppression to CD11b+Gr-1+ MDSC generated by melanoma, DC-HIL may be considered an activation marker for MDSC, akin to CD80/CD86 costimulatory receptors for immune-stimulatory APC, but with a completely polar effect.

Because CD80, CD86 (as ligands of CTLA-4), and PD-L1 are coinhibitory ligands that deliver negative signals to T cells through their corresponding receptors (Egen et al., 2002 and Keir et al., 2011), the inventors tested their potential as a mediator of MDSCs suppressor activity (Yang et al., 2006; Liu et al., 2008 and Liu et al., 2009). Using a melanoma mouse model, they showed MDSC to express CD80, CD86, and PD-L1 at levels similar or greater than DC-HIL. However, only the DC-HIL pathway was shown responsible for the T cell suppressor activity and the tumor-promoting effects of MDSC. This distinction was due to a discovered bidirectional signal, in which DC-HIL on the one hand activates SD-4-linked protein tyrosine phosphatase (CD148) in T cells (Chung et al., 2011), while on the other hand also transduces tyrosine phosphorylation of its ITAM-like motif (only one unit of ITAM) (Humphrey et al., 2005), leading to activation of the IFN-γ/NOS-2 cascade in MDSC. These results suggest cross-linking of DC-HIL on MDSC induces activation of Syk kinase (Lowell et al., 2011), which is a major signal mediator for ITAM that in turn leads us to theorize a requirement for preactivation of MDSC before it can exert its remarkable T cell-suppressive activity. By contrast, other ligands that lack authentic tyrosine-based signal motifs only induce a unidirectional signal via their T cell receptors (CTLA-4 and PD-1) (Carreno and Collins, 2002 and Sharpe et al., 2007).

One consequence of ligating DC-HIL/SD-4 on MDSC is secretion of IFN-γ critical to activation and T cell-suppressive activity of these cells, consistent with previous studies of MDSC isolated from mice with liver inflammation (Cripps et al., 2010) or with C26 colon carcinoma (Gallina et al., 2006). In the latter study, MDSC suppressor activity required IFN-γ expression by both MDSC and T cells: MDSC from IFN-γ-deficient mice lost suppressor activity, and MDSC from WT mice failed to exert such activity on T cells lacking the IFN-γ gene. The former finding supports the inventors' theory, whereas the latter outcome raises the possibility that T cell-derived IFN-γ regulates sensitivity of T cells to MDSC function. The inventors speculate that MDSC-secreted IFN-γ is internalized rapidly by MDSC (prior to any T cell effect) and activates its signal pathway by binding to nuclear receptors (intracellular activation) (Puddu et al., 2005). Indeed, density of IFN-γ nuclear receptors was reported greater than cell-surface receptors in some cells (MacDonald et al., 1986). On the other hand, T cell-derived IFN-γ may augment or maintain activated MDSC or sustain a high level of SD-4 expression by T cells.

Because DC-HIL in this model was expressed by at least 3 cell types (melanoma, APC, and MDSC), their each compartment could have influenced the outcomes. Thus, it was important to assess their respective contributions. Since the ability of anti-DC-HIL mAb to suppress melanoma growth was not diminished in mice bearing melanoma knocked-down for DC-HIL and since the same mAb did not enhance the APC capacity of DC injected into DC-HIL$^{-/-}$ mice, the inventors conclude that DC-HIL+ MDSC (and not DC-HIL+ melanoma nor DC-HIL+ APC) exerted the critical effect. This conclusion was also supported by in vitro assays showing deletion of DC-HIL to abrogate MDSC suppressor function completely, while only increasing melanoma-induced activation of T cells by 50% (Tomihari et al., 2010) and only augmenting APC capacity 2-fold. Also consistent with this conclusion is over-representation of DC-HIL+ MDSC within spleens of melanoma-bearing mice, contrasted with their very low frequencies in tumor-free mice. This is not to say DC-HIL+ melanoma cells or DC-HIL+ APC play no roles in tumor development, since both likely contribute importantly to initial phases of primary melanoma growth. However, the inventors believe that their effects become superseded by the progressively greater influence of exponentially expanding DC-HIL+ MDSC induced by the enlarging tumor.

Therapeutic agents targeting MDSC have been developed, including: all-trans retinoic acid (Lathers et al., 2004), which promotes MDSC differentiation to APC; the tyrosine kinase inhibitor sunitinib (Ko et al., 2009) that inhibits their metabolic process; COX-2 inhibitors (Rodriguez et al., 2005), Stat3 inhibitors (Xin 2009), and the phosphodiesterase-5 inhibitor (Sildanefil) (Serafini et al., 2006) which block or neutralize suppressor function. These agents improved efficacy of anti-tumor immunotherapy, but unlike the inventors' anti-DC-HIL mAb, none were specific for activated MDSC.

Humanized anti-CTLA-4 mAb (ipilimumab) is a recently developed treatment for metastatic melanoma that prolonged survival of patients with metastatic melanoma (Hodi et al., 2010). Ipilimumab augments T cell effects by blocking the coinhibitory function of CTLA-4. However, its benefits are limited by development of autoimmune disease causing dermatitis, hepatitis, colitis, and in some cases, death (51). Unlike DC-HIL, the CTLA-4 ligands CD80 and CD86 are not involved in MDSC function. CTLA-4 is present in all activated T cells and regulates development of autoreactive T cells via supporting $T_{reg}$ function (Gattinoni et al., 2006), whereas SD-4 is only expressed by effector T cells (Akiyoshi et al., 2010) and has no impact on $T_{reg}$ (unpublished data). Moreover, CTLA-4$^{-/-}$ mice die early from lymphoproliferative disease (Tivol et al., 1995), while DC-HIL$^{-/-}$ or SD-4$^{-/-}$ mice survive without observable autoimmune diseases (unpublished data). These differences suggest that strategies negating DC-HIL/SD-4 function may yield safer or better outcomes than those directed at CTLA-4.

In summary, blocking DC-HIL function inhibited growth of established melanoma and prevented MDSC expansion in mice, while restoring MDSC-suppressed T cell function in melanoma patients. These outcomes provide a strong incentive for developing treatment modalities that target DC-HIL-dependent pathway.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Bingisser et al., *J Immunol.*, 160(12):5729-5734, 1998.
Brown et al., *J Immunol. Meth.*, 12; 130(1), :111-121, 1990.
Campbell, In: *Monoclonal Antibody Technology, Laboratory Techniques in Biochemistry and* Capaldi et al., *Biochem. Biophys. Res. Comm.*, 74(2):425-433, 1977.
Carreno and Collins, *Annu Rev Immunol.*, 2029-53, 2002.
Cheng et al., *J Exp Med.*, 205(10):2235-2249, 2008.
Chung et al., *Blood.*, 109(10):4320-4327, 2007a.
Chung et al., *Eur J Immunol.*, 39(4):965-974, 2009.
Chung et al., *Eur J Immunol.*, 41(6):1794-1799, 2011.
Chung et al., *J Immunol.*, 179(9):5778-5784, 2007b.
Chung et al., *J Immunol.*, 183(8):5190-5198, 2009.
Cripps et al., *Hepatology.*, 52(4):1350-1359, 2010.
De Jager et al., *Semin. Nucl. Med.* 23(2), 165-179, 1993.
De Santo et al., *Proc Natl Acad Sci USA.*, 102(11):4185-4190, 2005.
Dholakia et al., *J. Biol. Chem.*, 264, 20638-20642, 1989.
Diaz-Montero et al., *Cancer Immunol Immunother.*, 58(1): 49-59, 2009.
Doolittle and Ben-Zeev, *Methods Mol. Biol.*, 109, 215-237, 1999.
Egen et al., *Nat Immunol.*, 3(7):611-618, 2002.
Elkabets et al., *Eur J Immunol.*, 40(12):3347-3357, 2010.
EP Application 125,023
EP Application 171,496
EP Application 173,494
EP Application 184,187
Filipazzi et al., *J Clin Oncol.*, 25(18):2546-2553, 2007.
Frey, *J Clin Invest.*, 116(10):2587-2590, 2006.
Gabrilovich et al., *Blood.*, 92(11):4150-4166, 1998.
Gabrilovichw and Nagaraj, *Nat Rev Immunol.*, 9(3):162-174, 2009.
Gallina et al., *J Clin Invest.*, 116(10):2777-2790, 2006.
Gattinoni et al., *Blood.*, 108(12):3818-3823, 2006.
Gefter et al., *Somatic Cell Genet.*, 3:231-236, 1977.
Goding, In: *Monoclonal Antibodies: Principles and Practice*, 2d ed., Orlando, Fla., Academic Press, pp. 60-61, 65-66, 71-74, 1986.
Gulbis and Galand, *Hum. Pathol.* 24(12), 1271-1285, 1993.
Guo et al., *Sci. Transl. Med.* 3:99 ra85, 2001.
Hodi et al., *N Engl J Med.*, 363(8):711-723, 2010.
Humphrey et al., *Immunol Rev.*, 20850-65, 2005.
Ishiguro et al., *J Biol Chem.*, 275(8):5249-5252, 2000.
Jones et al., *Nature*, 321:522-525, 1986.
Kamijo et al., *Science.*, 263(5153):1612-1615, 1994.
Keir et al., *Curr Opin Immunol.*, 19(3):309-314, 2007.
Khatoon et al., *Ann. of Neurology*, 26, 210-219, 1989.
Kim et al., *J Neurosci.*, 30(11):3933-3946, 2010.
King et al., *J Biol. Chem.*, 269, 10210-10218, 1989.
Kinlough et al., *J. Biol. Chem.*, 279(51):53071-53077, 2004.
Kinoshita et al., *Biochem. Biophys. Res. Commun.*, 394:205-210, 2010.
Ko et al., *Clin Cancer Res.*, 15(6):2148-2157, 2009.
Kohler and Milstein, *Eur. J. Immunol.*, 6, 511-519, 1976.
Kohler and Milstein, *Nature*, 256, 495-497, 1975.
Kusmartsev and Gabrilovich, *J Leukoc Biol.*, 74(2):186-196, 2003.
Kyte and Doolittle, *J. Mol. Biol.*, 157(1):105-132, 1982.
Lathers et al., *Cancer Immunol Immunother.*, 53(5):422-430, 2004.
Ligtenberg et al., *J Biol. Chem.*, 267, 6171-6177, 1992.
Liu et al., *Blood.*, 109(10):4336-4342, 2007.
Liu et al., *Cancer Immunol Immunother.*, 58(5):687-697, 2009.
Liu et al., *Clin Immunol.*, 129(3):471-481, 2008.
Lowell et al., *Cold Spring Harb Perspect Biol.*, 3(3), 2011.
MacDonald et al., *Biochem Biophys Res Commun.*, 138(1): 254-260, 1986.
Metz et al., *Breast Cancer Res.*, 9(5):R58, 2007.
Morrison, *Science*, 229(4719):1202-1207, 1985.
Movahedi et al., *Blood.*, 111(8):4233-4244, 2008.
Nagaraj et al., *Nat Med.*, 13(7):828-835, 2007.
Nakamura et al., In: *Enzyme Immunoassays: Heterogeneous and Homogeneous Systems*, O'Shannessy et al., *J. Immun. Meth.*, 99, 153-161, 1987.

Overwijk et al., *J Exp Med.*, 198(4):569-580, 2003.
Owens and Haley, *J Biol. Chem.*, 259:14843-14848, 1987.
PCT Application PCT/US86/02269
Peranzoni et al., *Curr Opin Immunol.*, 22(2):238-244, 2010.
Posner et al., *Hybridoma* 6, 611-625, 1987.
Potter and Haley, *Meth. Enzymol.*, 91, 613-633, 1983.
Puddu et al., *J Leukoc Biol.*, 78(3):686-695, 2005.
Remington's Pharmaceutical Sciences, 15th Ed., 3:624-652, 1990.
Rodriguez and Ochoa, Immunol Rev., 222180-191, 2008.
Rodriguez et al., *J Exp Med.*, 202(7):931-939, 2005.
Safadi et al., *J Cell Biochem.*, 84(1):12-26, 2001.
Serafini et al., *Cancer Res.*, 68(13):5439-5449, 2008.
Serafini et al., *J Exp Med.*, 203(12):2691-2702, 2006.
Serafini et al., *Semin Cancer Biol.*, 16(1):53-65, 2006.
Sharpe et al., *Nat Immunol.*, 8(3):239-245, 2007.
Shaw et al., *J. Natl. Cancer Inst.*, 80(19):1553-1559, 1988.
Shikano et al., *J Biol Chem.*, 276(11):8125-8134, 2001.
Sinha et al., *J Immunol.*, 179(2):977-983, 2007.
Sun et al., *J. Steroid Biochem.*, 26(1):83-92, 1987.
Tang et al., *J. Biol. Chem.*, 271:28324-28330, 1996.
Tivol et al., *Immunity.*, 3(5):541-547, 1995.
Tomihari et al., *Cancer Res.*, 70(14):5778-5787, 2010.
Verhoeyen et al., *Science*, 239(4847):1534-1536, 1988.
Wang et al., *Eur J Immunol.*, 40(9):2569-2579, 2010.
Weterman et al., *Int J Cancer.*, 60(1):73-81, 1995.
Wood et al., *J. Clin. Lab. Immunol.*, 17(4):167-171, 1985.
Xin et al., *Cancer Res.*, 69(6):2506-2513, 2009.
Yang et al., *Cancer Res.*, 66(13):6807-6815, 2006.

What is claimed is:

1. A method of predicting the progression of melanoma in a subject comprising:
    (a) obtaining a sample from said subject; and
    (b) using an antibody-based immunoassay to determine in said sample:
        (i) a DC-HIL level on myeloid-derived suppressor cells (MDSCs) in said subject; or
        (ii) the number of DC-HIL-positive MDSCs;
    wherein a higher level of DC-HIL on said MDSCs of step (b)(i) as compared to an MDSC from a non-cancer subject, or a higher number of DC-HIL-positive MDSCs in step (b)(ii), as compared to a non-cancer subject, indicates that said subject will have progression of melanoma, and
    wherein the antibody comprises light chain CDR sequences SEQ ID NOS: 1, 2 and 3 and heavy chain CDR sequences SEQ ID NOS: 4, 5 and 6.

2. The method of claim 1, wherein said sample is a tumor biopsy, blood or serum.

3. The method of claim 1, further comprising performing steps (a) and (b) a second time and determining a change from the level or number from the previous assay.

4. The method of claim 1, wherein the antibody is a recombinant ScFv (single chain fragment variable) antibody, Fab fragment, F(ab')$_2$ fragment, or Fv fragment.

5. A method of predicting the response of a subject to melanoma immunotherapy comprising:
    (a) obtaining a sample from said subject; and
    (b) using an antibody-based immunoassay to determine in said sample:
        (i) a DC-HIL level on myeloid-derived suppressor cell (MDSCs) in said subject; or
        (ii) the number of DC-HIL-positive MDSCs;
    wherein a lower level of DC-HIL on said MDSCs of step (b)(i) as compared to a level in a non-cancer subject, or a lower number of DC-HIL-positive MDSCs in step (b)(ii), as compared to a non-cancer subject, indicates that said subject will have a response to melanoma immunotherapy, and
    wherein the antibody comprises light chain CDR sequences SEQ ID NOS: 1, 2 and 3 and heavy chain CDR sequences SEQ ID NOS: 4, 5 and 6.

6. The method of claim 5, wherein said sample is a tumor biopsy, blood or serum.

7. The method of claim 5, further comprising performing steps (a) and (b) a second time and determining a change from the level or number from the previous assay, wherein a lower level of DC-HIL on said MDSCs of step (b)(i) as compared to a previously measured level, or a lower number of DC-HIL-positive MDSCs in step (b)(ii), as compared to a previously measured number, indicates that said subject is responding to an intervening melanoma immunotherapy.

8. The method of claim 5, wherein the antibody is a recombinant ScFv (single chain fragment variable) antibody, Fab fragment, F(ab')$_2$ fragment, or Fv fragment.

* * * * *

```
                         SEQUENCE LISTING

<160> NUMBER OF SEQ ID NOS: 32

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Ser Ser Ile Ser Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 2

Thr Thr Ser
1

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

His Gln Ser Ser Ser Tyr Pro Tyr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Gly Tyr Thr Phe Thr Asn Tyr Tyr
1               5

<210> SEQ ID NO 5
<211> LENGTH: 8
<212> TYPE: PRT
<213> ORGANISM: Artificial Sequence
<220> FEATURE:
```

<223> OTHER INFORMATION: Synthetic Peptide

<400> SEQUENCE: 5

Ile Asn Thr Arg Asn Gly Gly Asn
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 6

Thr Thr Gly Phe Ala Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

His Gln Ser Ser Ser His Pro Tyr Thr
1               5

<210> SEQ ID NO 8
<211> LENGTH: 125
<212> TYPE: PRT
<213> ORGANISM: Artificial Sequence
<220> FEATURE:
<223> OTHER INFORMATION: Synthetic peptide

<400> SEQUENCE: 8

Val Ser Phe Leu Leu Ile Ser Ala Ser Val Ile Met Ser Arg Gly Gln
1               5                   10                  15

Ile Val Leu Thr Gln Ser Pro Ala Ile Met Ser Ala Ser Leu Gly Glu
                20                  25                  30

Glu Ile Thr Leu Thr Cys Ser Ala Ser Ser Ser Ile Ser Tyr Met His
            35                  40                  45

Trp Tyr Gln Gln Lys Ser Gly Thr Ser Pro Lys Leu Leu Ile Tyr Thr
    50                  55                  60

Thr Ser Thr Leu Ser Ser Gly Val Pro Ser Arg Phe Ser Gly Ser Gly
65                  70                  75                  80

Ser Gly Thr Phe Tyr Ser Leu Thr Ile Ser Val Glu Ala Glu Asp Ala
                85                  90                  95

Ala Ala Asp Tyr Tyr Cys His Gln Ser Ser Ser Tyr Pro Tyr Thr Phe
            100                 105                 110

Gly Gly Gly Thr Lys Leu Glu Ile Lys Arg Ala Asp Ala
        115                 120                 125

<210> SEQ ID NO 9
<211> LENGTH: 119
<212> TYPE: PRT
<213> ORGANISM: Artificial Sequence
<220> FEATURE:
<223> OTHER INFORMATION: Synthetic peptide

<400> SEQUENCE: 9

Thr Thr Gly Val His Ser Gln Val Gln Leu Gln Gln Ser Gly Ala Glu
1               5                   10                  15

Leu Val Lys Pro Gly Thr Ser Val Lys Leu Ser Cys Lys Ala Ser Gly
            20                  25                  30

Tyr Thr Phe Thr Asn Tyr Tyr Met Tyr Trp Val Lys Gln Arg Pro Gly
            35                  40                  45

Gln Gly Leu Glu Trp Ile Gly Glu Ile Asn Thr Arg Asn Gly Gly Asn
50                      55                  60

Arg Phe Asn Glu Lys Phe Lys Asn Lys Ala Ile Leu Thr Val Asp Lys
65                  70                  75                  80

Ser Ser Asn Thr Ala Tyr Ile Gln Val Ser Ser Leu Thr Ser Glu Asp
                85                  90                  95

Ser Ala Val Tyr Tyr Cys Thr Thr Gly Phe Ala Tyr Trp Gly Gln Gly
            100                 105                 110

Thr Leu Val Thr Val Ser Ala
            115

<210> SEQ ID NO 10
<211> LENGTH: 125
<212> TYPE: PRT
<213> ORGANISM: Artificial Sequence
<220> FEATURE:
<223> OTHER INFORMATION: Synthetic peptide

<400> SEQUENCE: 10

Val Ser Phe Leu Leu Ile Ser Ala Ser Val Ile Met Ser Arg Gly Gln
1               5                   10                  15

Ile Val Leu Thr Gln Ser Pro Ala Ile Met Ser Ala Ser Leu Gly Glu
            20                  25                  30

Glu Ile Thr Leu Thr Cys Ser Ala Ser Ser Ser Ile Ser Tyr Met His
            35                  40                  45

Trp Tyr Gln Gln Lys Ser Gly Thr Ser Pro Lys Leu Leu Ile Tyr Thr
50                  55                  60

Thr Ser Thr Leu Ser Ser Gly Val Pro Ser Arg Phe Ser Gly Ser Gly
65                  70                  75                  80

Ser Gly Thr Phe Tyr Ser Leu Thr Ile Ser Ser Val Glu Ala Glu Asp
                85                  90                  95

Ala Ala Asp Tyr Tyr Cys His Gln Ser Ser His Pro Tyr Thr Phe
            100                 105                 110

Gly Gly Gly Thr Lys Leu Glu Ile Lys Arg Ala Asp Ala
            115                 120                 125

<210> SEQ ID NO 11
<211> LENGTH: 119
<212> TYPE: PRT
<213> ORGANISM: Artificial Sequence
<220> FEATURE:
<223> OTHER INFORMATION: Synthetic peptide

<400> SEQUENCE: 11

Thr Thr Gly Val His Ser Gln Val Gln Leu Gln Gln Ser Gly Ala Glu
1               5                   10                  15

Leu Val Lys Pro Gly Thr Ser Val Lys Leu Ser Cys Lys Ala Ser Gly
            20                  25                  30

Tyr Thr Phe Thr Asn Tyr Tyr Met Tyr Trp Val Lys Gln Arg Pro Gly
            35                  40                  45

Gln Gly Leu Glu Trp Ile Gly Glu Ile Asn Thr Arg Asn Gly Gly Asn
50                  55                  60

Arg Phe Asn Glu Lys Phe Lys Asn Lys Ala Ile Leu Thr Val Asp Lys

```
                        65                  70                  75                  80
Ser Ser Asn Thr Ala Tyr Ile Gln Val Ser Ser Leu Thr Ser Glu Asp
                85                  90                  95

Ser Ala Val Tyr Tyr Cys Thr Thr Gly Phe Ala Tyr Trp Gly Gln Gly
            100                 105                 110

Thr Leu Val Thr Val Ser Ala
        115

<210> SEQ ID NO 12
<211> LENGTH: 354
<212> TYPE: DNA
<213> ORGANISM: Artificial Sequence
<220> FEATURE:
<223> OTHER INFORMATION: Synthetic nucleotide

<400> SEQUENCE: 12
gcctcagtca taatgtccag aggacaaatt gttctcaccc agtctccagc aatcatgtct      60
gcatctctag gggaggagat caccctaacc tgcagtgcca gttcgagtat aagttacatg     120
cactggtacc agcagaagtc aggcacttct cccaaactct tgatttatac cacatccacc     180
ctgtcttctg gagtcccttc tcgcttcagt ggcagtgggt ctgggacctt ttattctctc     240
acaatcagca gtgtggaggc tgaagatgct gccgattatt actgccatca gtcgagtagt     300
tatccgtata cattcggagg ggggaccaag ctggaaataa acgggctga tgct            354

<210> SEQ ID NO 13
<211> LENGTH: 339
<212> TYPE: DNA
<213> ORGANISM: Artificial Sequence
<220> FEATURE:
<223> OTHER INFORMATION: Synthetic nucleotide

<400> SEQUENCE: 13
caggtccaac tgcagcagtc tggggctgaa ctggtgaagc ctgggacttc agtgaagttg      60
tcctgcaagg cttctggcta caccttcacc aactactata tgtactgggt gaaacagagg     120
cctggacaag gccttgagtg gattggagag attaatacta gaaatggtgg taataggttc     180
aatgagaagt tcaagaacaa ggccatattg actgtagaca atcctccaa cacagcatac     240 atacaagtca gcagcctgac atctgaggac tctgcggtct attactgtac tacggggttt     300
gcttactggg gccaagggac tctggtcact gtctctgca                             339

<210> SEQ ID NO 14
<211> LENGTH: 354
<212> TYPE: DNA
<213> ORGANISM: Artificial Sequence
<220> FEATURE:
<223> OTHER INFORMATION: Synthetic nucleotide

<400> SEQUENCE: 14
gcctcagtca taatgtccag aggacaaatt gttctcaccc agtctccagc aatcatgtct      60
gcatctctag gggaggagat caccctaacc tgcagtgcca gttcgagtat aagttacatg     120
cactggtacc agcagaagtc aggcacttct cccaaactct tgatttatac cacatccacc     180
ctgtcttctg gagtcccttc tcgcttcagt ggcagtgggt ctgggacctt ttattctctc     240
acaatcagca gtgtggaggc tgaagatgct gccgattatt actgccatca gtcgagtagt     300
catccgtata cattcggagg ggggaccaag ctggaaataa acgggctga tgct            354

<210> SEQ ID NO 15
```

<211> LENGTH: 339
<212> TYPE: DNA
<213> ORGANISM: Artificial Sequence
<220> FEATURE:
<223> OTHER INFORMATION: Synthetic nucleotide

<400> SEQUENCE: 15

```
caggtccaac tgcagcagtc tggggctgaa ctggtgaagc ctgggacttc agtgaagttg      60
tcctgcaagg cttctggcta caccttcacc aactactata tgtactgggt gaaacagagg     120
cctggacaag gccttgagtg gattggagag attaatacta gaaatggtgg taataggttc     180
aatgagaagt tcaagaacaa ggccatattg actgtagaca atcctccaa cacagcatac      240
atacaagtca gcagcctgac atctgaggac tctgcggtct attactgtac tacggggttt     300
gcttactggg gccaagggac tctggtcact gtctctgca                            339
```

<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Lys Arg Phe Arg
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide

<400> SEQUENCE: 17

Ile Thr Ala Met
1

<210> SEQ ID NO 18
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 18

Tyr Xaa Xaa Ile
1

<210> SEQ ID NO 19
<211> LENGTH: 4
<212> TYPE: PRT
<213> ORGANISM: Artificial sequence
<220> FEATURE:
<223> OTHER INFORMATION: Synthetic peptide

<400> SEQUENCE: 19

Lys Arg Phe His
1

<210> SEQ ID NO 20
<211> LENGTH: 18

```
<212> TYPE: DNA
<213> ORGANISM: Artificial sequence
<220> FEATURE:
<223> OTHER INFORMATION: Synthetic primer

<400> SEQUENCE: 20
rctacaggtg tccactcc                                                    18

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
tagcccttga ccaggcatcc                                                  20

<210> SEQ ID NO 22
<211> LENGTH: 21
<212> TYPE: DNA
<213> ORGANISM: Artificial sequence
<220> FEATURE:
<223> OTHER INFORMATION: Synthetic primer

<400> SEQUENCE: 22
tcagcttcyt gctaatcagt g                                                21

<210> SEQ ID NO 23
<211> LENGTH: 20
<212> TYPE: DNA
<213> ORGANISM: Artificial sequence
<220> FEATURE:
<223> OTHER INFORMATION: Synthetic primer

<400> SEQUENCE: 23
tggtgggaag atggatacag                                                  20

<210> SEQ ID NO 24
<211> LENGTH: 20
<212> TYPE: DNA
<213> ORGANISM: Artificial sequence
<220> FEATURE:
<223> OTHER INFORMATION: Synthetic primer

<400> SEQUENCE: 24
agtggagcag gtgaagagtg                                                  20

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
ttcggagaga ggtacaaacg                                                  20

<210> SEQ ID NO 26
<211> LENGTH: 21
<212> TYPE: DNA
<213> ORGANISM: Artificial sequence
<220> FEATURE:
<223> OTHER INFORMATION: Synthetic primer

<400> SEQUENCE: 26
```
tgtgctttga tggagatgag g                                              21

<210> SEQ ID NO 27
<211> LENGTH: 22
<212> TYPE: DNA
<213> ORGANISM: Artificial sequence
<220> FEATURE:
<223> OTHER INFORMATION: Synthetic primer

<400> SEQUENCE: 27
caaagttgtc tctgaggtct gg                                             22

<210> SEQ ID NO 28
<211> LENGTH: 19
<212> TYPE: DNA
<213> ORGANISM: Artificial sequence
<220> FEATURE:
<223> OTHER INFORMATION: Synthetic primer

<400> SEQUENCE: 28
agagtgaaaa gtccagccg                                                 19

<210> SEQ ID NO 29
<211> LENGTH: 20
<212> TYPE: DNA
<213> ORGANISM: Artificial sequence
<220> FEATURE:
<223> OTHER INFORMATION: Synthetic primer

<400> SEQUENCE: 29
acaactcgct ccaagattcc                                                20

<210> SEQ ID NO 30
<211> LENGTH: 21
<212> TYPE: DNA
<213> ORGANISM: Artificial sequence
<220> FEATURE:
<223> OTHER INFORMATION: Synthetic primer

<400> SEQUENCE: 30
ctgccacctg atcctaactt g                                              21

<210> SEQ ID NO 31
<211> LENGTH: 21
<212> TYPE: DNA
<213> ORGANISM: Artificial sequence
<220> FEATURE:
<223> OTHER INFORMATION: Synthetic primer

<400> SEQUENCE: 31
cagccaaaca ccaaagtcat g                                              21

<210> SEQ ID NO 32
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 32

Tyr Xaa Tyr Ile
1